United States Patent
Klee et al.

(10) Patent No.: US 10,532,009 B2
(45) Date of Patent: Jan. 14, 2020

(54) DENTAL COMPOSITION

(71) Applicant: DENTSPLY SIRONA inc., York, PA (US)

(72) Inventors: Joachim Klee, Radolfzell (DE); Maximilian Maier, Dusseldorf (DE); Jacques Lalevee, Mulhouse (FR); Christoph P. Fik, Schonenberg a.d. Thur (CH); Jean Pierre Fouassier, St. Hippolyte (FR); Fabrice Morlet-Savary, Pfastatt (FR); Celine Dietlin, Mulhouse (FR)

(73) Assignee: DENTSPLY SIRONA Inc., York, PA (US)

( * ) Notice: Subject to any disclaimer, the term of this patent is extended or adjusted under 35 U.S.C. 154(b) by 14 days.

(21) Appl. No.: 15/562,497

(22) PCT Filed: Mar. 30, 2016

(86) PCT No.: PCT/EP2016/056874
§ 371 (c)(1),
(2) Date: Sep. 28, 2017

(87) PCT Pub. No.: WO2016/156363
PCT Pub. Date: Oct. 6, 2016

(65) Prior Publication Data
US 2018/0092811 A1    Apr. 5, 2018

(30) Foreign Application Priority Data

Mar. 30, 2015 (EP) .......................... 1516747
Jun. 12, 2015 (EP) .......................... 1517926

(51) Int. Cl.
*A61K 6/083* (2006.01)
*A61K 6/00* (2006.01)
(Continued)

(52) U.S. Cl.
CPC ............ *A61K 6/083* (2013.01); *A61K 6/0023* (2013.01); *A61K 6/0052* (2013.01);
(Continued)

(58) Field of Classification Search
None
See application file for complete search history.

(56) References Cited

U.S. PATENT DOCUMENTS 3,534,122 A * 10/1970 Cornell ................. C08F 265/06
525/222
4,116,788 A * 9/1978 Schmitt ................... C08K 5/524
260/998.11
(Continued)

FOREIGN PATENT DOCUMENTS

| WO | 2009147033 A1 | 12/2009 |
| WO | 2012045736 A1 | 4/2012 |
| WO | 2014060450 A1 | 4/2014 |

OTHER PUBLICATIONS

International Search Report dated Apr. 29, 2016.
(Continued)

*Primary Examiner* — Peter A Salamon
(74) *Attorney, Agent, or Firm* — Dentsply Sirona Inc.

(57) ABSTRACT

Disclosed herein is a dental composition having a polymerization initiator system with an aromatic tertiary phosphine compound. Further disclosed is the use of the aromatic tertiary phospine compound for the preparation of a photocurable dental compositions.

13 Claims, 11 Drawing Sheets

(51) Int. Cl.
*A61K 6/033* (2006.01)
*C08L 33/08* (2006.01)
*C08L 33/10* (2006.01)
*C07F 9/50* (2006.01)
*C08F 2/50* (2006.01)

(52) U.S. Cl.
CPC ............ *A61K 6/0073* (2013.01); *A61K 6/033* (2013.01); *C08L 33/08* (2013.01); *C08L 33/10* (2013.01); *C07F 9/5022* (2013.01); *C08F 2/50* (2013.01)

(56) References Cited

U.S. PATENT DOCUMENTS

| | | | | |
|---|---|---|---|---|
| 4,595,753 | A * | 6/1986 | Oswald | C07C 45/49 546/2 |
| 4,668,809 | A * | 5/1987 | Oswald | C07C 45/49 556/18 |
| 4,687,866 | A * | 8/1987 | Oswald | C07C 45/50 556/18 |
| 4,687,874 | A * | 8/1987 | Oswald | C07C 45/49 568/454 |
| 5,202,304 | A * | 4/1993 | Iwakura | B41M 5/155 503/209 |
| 5,532,373 | A * | 7/1996 | Matsumoto | G03F 7/029 430/281.1 |
| 5,545,676 | A * | 8/1996 | Palazzotto | A61K 6/083 430/270.1 |
| 5,852,067 | A * | 12/1998 | Sukejima | C08F 283/01 522/53 |
| 6,187,836 | B1 * | 2/2001 | Oxman | A61K 6/0017 522/100 |
| 9,864,103 | B2 * | 1/2018 | Wang | G02B 1/043 |
| 2012/0129097 | A1 * | 5/2012 | Choi | G03F 7/033 430/281.1 |
| 2012/0196952 | A1 * | 8/2012 | Suzuki | A61K 6/0023 523/116 |
| 2012/0216488 | A1 * | 8/2012 | Liu | G02B 1/043 53/425 |
| 2012/0216489 | A1 * | 8/2012 | Lee | B29D 11/00038 53/428 |
| 2012/0218509 | A1 * | 8/2012 | Back | C08L 83/04 351/159.33 |
| 2012/0220690 | A1 * | 8/2012 | Liu | G02B 1/043 523/107 |
| 2012/0220743 | A1 * | 8/2012 | Francis | C08F 230/08 526/279 |
| 2012/0220744 | A1 * | 8/2012 | Liu | G02B 1/043 526/279 |
| 2012/0244366 | A1 * | 9/2012 | Kuruma | A61L 29/085 428/461 |
| 2013/0158157 | A1 | 6/2013 | Stelzig | |
| 2013/0176530 | A1 * | 7/2013 | Goodenough | G02C 7/04 351/159.33 |
| 2014/0009735 | A1 * | 1/2014 | Zheng | G02B 1/043 351/159.33 |
| 2014/0016086 | A1 * | 1/2014 | Liu | G02B 1/043 351/159.33 |
| 2014/0018465 | A1 * | 1/2014 | Liu | G02B 1/043 523/107 |
| 2014/0024738 | A1 * | 1/2014 | Chen | G02B 1/043 523/107 |
| 2016/0068669 | A1 * | 3/2016 | MacFarlane | C08L 25/06 524/505 |
| 2018/0092811 | A1 * | 4/2018 | Klee | A61K 6/0023 |

OTHER PUBLICATIONS

Jacques Lalevee et al: "Germanes as efficient coinitiators in radical and cationic photopolymerizations", Journal of Polymer Science Part A: Polymer Chemistry, vol. 46, No. 9, May 1, 2008 (May 1, 2008), pp. 3042-3047, XP055269712, US ISSN:0887-624X, DOI: 10.1002/pola.22644 abstract p. 3044, Results and discussion to p. 3047 conclusions.

J. Lalevee et al: "Silanes as New Highly Efficient Co-initiators for Radical Polymerization in Aerated Media", Macromolecules, vol. 41, No. 6, Mar. 1, 2008 (Mar. 1, 2008), pp. 2003-2010, XP055139430, ISSN: 0024-9297, DOI: 10.1021/ma702301x p. 2004, Schema 2, compounds 1a-1h; p. 2006, table 3; p. 2006, table 3; p. 2006, left-handcol. par.3, p. 2006, right-hand col. par. (iii).

* cited by examiner

DENTAL COMPOSITION

FIELD OF THE INVENTION

The present invention relates to a dental composition comprising a specific polymerization initiator system comprising an aromatic tertiary phosphine compound. The present invention also relates to the use of said aromatic tertiary phosphine compound for the preparation of a photocurable dental composition.

BACKGROUND OF THE INVENTION

The restoration of teeth commonly involves a light curable dental composition containing free-radically polymerizable resins. Light curing of a dental composition involves a photoinitiator system generating free radicals upon exposure to visible light. Free radicals may be typically produced by either of two pathways:
(1) the photoinitiator compound undergoes excitation by energy absorption with subsequent decomposition of the compound into one or more radicals (Norrish type I), or
(2) the photoinitiator compound undergoes excitation and the excited photoinitiator compound interacts with a second compound by either energy transfer or a redox reaction to form free radicals from any of the compounds (Norrish type II).

In order for a photoinitiator to be useful for use in a dental composition, the quantum yields indicating the conversion of light radiation to radical formation needs to be high since absorption or shielding of light by further components of the dental composition limit the amount of energy available for absorption by the photoinitiators. Accordingly, only about 70 percent conversion of the polymerizable groups may be expected in a polymerization of a typical dental composition, whereby the mechanical strength of the polymerized dental composition is less than optimal and unreacted monomers may leach out of the the polymerized dental composition. The leaching monomers may have detrimental effects. In order to alleviate this problem, multifunctional monomers are frequently used which are more likely to be included in the polymer network.

In addition, photoinitiators are required to have a high acid resistance, solubility, thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the polymerization initiator system has a critical influence on the quality of the dental material. Conventionally, camphor quinone optionally in combination with a tertiary amine, or 2, 4, 6-trimethylbenzoylphenyl phosphinate (Irgacure® TPO) are frequently used as photoinitiator system. However, the presence of amines in acrylate-containing compositions can cause yellowing in the resulting photocured composition, create undesirable odors, and soften the cured composition because of chain transfer reactions and therefore, often require the use of stabilizers. Moreover, the use of aromatic amines gives rise to toxicological concerns.

Furthermore, it is desirable that the light activating the photoinitiator system has a long wavelength in order to avoid damage of soft tissue during polymerization of the dental composition in the patient's mouth. Accordingly, the photoinitiator system is required to contain a chromophoric group efficiently absorbing light of the desired wavelength in a range of from 400 to 800 nm. However, an increase of the absorption coefficient of the photoinitiator system increases the coloration of the photoinitiator system and thereby the coloration of the dental composition before light curing. Accordingly, it is necessary that the chromophoric groups are efficiently destroyed during polymerization so that the coloration of the initiator system disappears in the polymerized dental composition, the so-called "photobleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers.

U.S. Pat. No. 3,534,122 discloses a free radical polymerizable composition containing liquid monomeric acrylate and methacrylate esters of monohydric and polyhydric alcohols. A tertiary organo-phosphine promoter is disclosed for accelerating polymerization chemically initiated by monotertiary butyl peroxy permaleate.

WO 2009/147033 A1 discloses a photoinitiator mixture comprising at least one specific alpha-amine ketone compound and at least one specific oxime ester compound. WO 2012/045736 A1 discloses benzocarbazole derivatives as photoinitiator. WO 2014/060450 A1 discloses combinations of phenylglyoxylic acid compounds with alpha-hydroxyketones as photoinitiators. Phosphorus compounds, for example triphenylphosphine, are mentioned as additive for increasing the stability on storage in the dark.

U.S. Pat. No. 5,545,676 discloses a ternary photoinitiator system for addition polymerization which comprises an aryliodonium salt, a sensitizing compound and a specific electron donor. Triphenylphosphine is disclosed in combination with CQ. Specifically, U.S. Pat. No. 5,545,676 discloses a composition obtained by adding equimolar amounts of triphenylphosphine were to a monomer stock solution containing 50 parts trimethylolpropane trimethacrylate, 50 parts 1,4-butanediol dimethacrylate, 0.25 part CPQ and optionally 0.5 part of the iodonium salt diphenyliodonium hexafluorophosphate. Triphenylphosphine is not preferred for lack of an abstractable hydrogen atom on a carbon or silicon atom alpha to the donor atom, which is reflected by the experimental results reported.

U.S. Pat. No. 6,187,836 discloses compositions featuring cationically active and free radically active functional groups. U.S. Pat. No. 6,187,836 discloses triphenylphosphine as cationic polymerization modifier. Specifically, U.S. Pat. No. 6,187,836 discloses a composition obtained by combining 10.0 g of a stock solution with a sufficient amount of a cationic polymerization modifier to achieve a modifier concentration of $1.13 \times 10^{-4}$ moles per 10.0 g of stock solution wherein the stock solution is obtained by combining 5.0 g camphorquinone (CPQ) and 15.0 g diaryliodonium hexafluoroantimonate (CD1012 from Sartomer) with 720.0 g Cyracure® UVR 6105 cycloaliphatic diepoxide resin (available from Union Carbide), 180.0 g of a polytetrahydrofuran diol having an average molecular weight of 250 (p-THF-250, available from Aldrich Chemical Co.), and 100 g of acrylate oligomer (Ebecryl 1830, available from UCB Radcure, Inc.)), and stirring until homogeneous under safe light conditions.

SUMMARY OF THE INVENTION

It is the problem of the present invention to provide an improved dental composition comprising one or more compounds having a polymerizable double bond, which composition provides
improved polymerization efficiency including a high conversion and good curing rate which may be adapted to provide a suitable working time of the composition,
high storage stability,
absence of coloration problems, and
which is applicable in acidic systems, so that the mechanical strength of the dental composition and the aesthetic properties may be improved as well as the adhesion of the polymerized dental composition to enamel and dentin.

Moreover, it is the problem of the present invention to provide a use of a specific compound for the preparation of a dental composition.

The present invention provides a dental composition comprising
(a) one or more compounds having at least one polymerizable double bond;
(b) a polymerization initiator system comprising
(b1) a sensitizer; and
(b2) an aromatic tertiary phosphine compound of the following formula (I):

Z—R      (I)

wherein
Z is a group of the following formula (II)

wherein
R$^1$ represents a substituted or unsubstituted hydrocarbyl group;
Ar represents a substituted or unsubstituted aryl or heteroaryl group;
R is an aryl group, which may be substituted by one or more groups selected from a hydroxyl group, an amino group, a —NR$^2$R$^3$ group (wherein R$^2$ and R$^3$, which may be the same or different, are selected from C$_{1-6}$ alkyl groups), a carboxyl group, and a group having a polymerizable double bond;
wherein the group R$^1$ and Ar may be substituted by one or more groups selected from a hydroxyl group, an oxo group, a —NR$^2$R$^3$ group (wherein R$^2$ and R$^3$, which may be the same or different, are selected from a hydrogen atom and C$_{1-6}$ alkyl groups), a carboxyl group, and a group having a polymerizable double bond, and
L may be substituted by one or more groups selected from a hydroxyl group, an oxo group, a —NR$^2$R$^3$ group (wherein R$^2$ and R$^3$, which may be the same or different, are selected from a hydrogen atom and C$_{1-6}$ alkyl groups), a carboxyl group, and a group having a polymerizable double bond.

Furthermore, the present invention provides the use of an aromatic phosphine compound of the following formula (I)

Z—R      (I)

wherein
Z is a group of the following formula (II)

wherein
R$^1$ represents a substituted or unsubstituted hydrocarbyl group;
Ar represents a substituted or unsubstituted aryl or heteroaryl group;
R is an aryl group, which may be substituted by one or more groups selected from a hydroxyl group, an amino group, a —NR$^2$R$^3$ group (wherein R$^2$ and R$^3$, which may be the same or different, are selected from C$_{1-6}$ alkyl groups), a carboxyl group, and a group having a polymerizable double bond;
wherein the group W and Ar may be substituted by one or more groups selected from a hydroxyl group, a —NR$^2$R$^3$ group (wherein R$^2$ and R$^3$, which may be the same or different, are selected from a hydrogen atom and C$_{1-6}$ alkyl groups), a carboxyl group, and a group having a polymerizable double bond, and
L may be substituted by one or more groups selected from a hydroxyl group, an oxo group, a —NR$^2$R$^3$ group (wherein R$^2$ and R$^3$, which may be the same or different, are selected from a hydrogen atom and C$_{1-6}$alkyl groups), a carboxyl group, and a group having a polymerizable double bond,
for the preparation of a dental composition.

The present invention is based on the recognition that an aromatic tertiary phosphine compound according to the present invention provides improved polymerization efficiency, high curing speed and high storage stability, and does not give rise to coloration problems of a dental composition. Accordingly, a relatively large amount of the dental composition can be photocured with reduced exposure to radiation. Due to the high efficiency of the photoinitiator compound, the presence of oxygen, or oxygen inhibition, is not a serious detriment during photocuring of a dental composition according to the present invention.

BRIEF DESCRIPTION OF THE FIGURES

FIG. 5a: camphorquinone (CQ)/ethyldimethylaminobenzoate (EDB) 0.4%/0.6% w/w or CQ/EDB/triphenyl phosphine (TPP) 0.4%/0.6%/1% w/w;

FIG. 5b: CQ/EDB 1%/1% w/w or CQ/EDB/4-(diphenylphosphino)styrene (DPPS) 1%/1%/1% w/w (for fresh formulation and after 2 months of storage at room temperature);

FIG. 5c: CQ/EDB/Diphenyliodonium hexafluorophosphate 1.2%/1%/1% w/w or CQ/EDB/diphenyliodonium hexafluorophosphate/TPP 1.2%/1%/1%/1% w/w.

DETAILED DESCRIPTION OF PREFERRED EMBODIMENTS

Figure 1A:
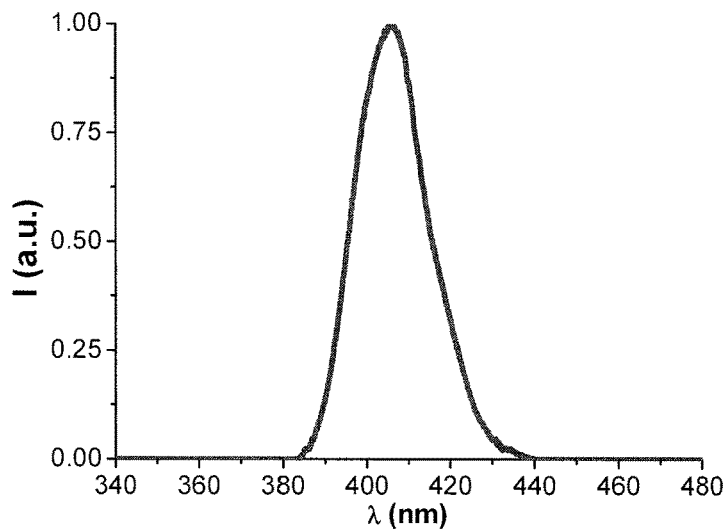
FIGS. 1a and 1b show the emission spectra of the irradiation sources used for the irradiation of the photocurable samples, namely a light emitting diode (LED) centred at 405 nm (M405L2 from ThorLabs; about 1100 mW/cm$^2$) and a blue dental LED centred at 477 nm (SmartLite® Focus from Dentsply, about 1000 mW/cm$^2$).

The term "polymerization" relates to the combining by covalent bonding of a large number of smaller molecules, such as monomers, to form larger molecules, that is, macromolecules or polymers. The monomers may be combined to form only linear macromolecules or they may be combined to form three-dimensional macromolecule, commonly referred to as crosslinked polymers. In case of a higher conversion rate of the polymerizable monomer, the amount of multifunctional monomers may be reduced or the leaching problem may be alleviated.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

The terms "photocurable" and "curable" refer to a dental composition that will polymerize into a crosslinked polymer network when irradiated for example with actinic radiation such as ultraviolet (UV), visible, or infrared radiation.

The term "quantum yield" is used herein to indicate the efficiency of a photochemical process. More particularly, quantum yield is a measure of the probability of the excitation of a particular molecule after absorption of a light quantum. The term expresses the number of photochemical events per photon absorbed.

"Actinic radiation" is any electromagnetic radiation that is capable of producing photochemical action and can have a wavelength of at least 150 nm and up to and including 1250 nm, and typically at least 300 nm and up to and including 750 nm.

The term "polymerizable double bound" as used herein in connection with compound(s) (a) and compound(s) (b2) means any double bond capable of radical polymerization, preferably a carbon-carbon double bond. Examples of the polymerizable double bond include vinyl, conjugated vinyl, allyl, acryl, methacryl and styryl. More preferably, the polymerizable double bound is selected from the group consisting of acryl, methacryl and styryl. Acryl and methacryl may be (meth)acryloyl or (meth)acrylamide. Most preferably, for the compound(s) (a), the polymerizable double bound is acryl or methacryl, and for the compound (b2), the polymerizable double bond with which groups $R^1$ and Ar and/or R and L may be substituted is preferably styryl.

The term "sensitizer" refers to a molecule that produces a chemical change in another molecule such as a photoinitiator in a photochemical process.

The term "photoinitiator" is any chemical compound that forms free radicals when activated, e. g. by exposure to light or interaction with a sensitizer in a photochemical process.

The term "polymerization initiator system" refers to a system comprising at least one sensitizer (b1) and at least one an aromatic tertiary phosphine compound (b2). Optionally, the polymerization initiator system may further comprise (b3) an electron-donor. According to a preferred embodiment, the polymerization initiator system contains or consists of a first sensitizer (b1-a) selected from an 1,2-diketone, and a second sensitizer (b1-b) selected from iodonium salts. In case of a substituted aromatic tertiary phosphine compound, the presence of an aryliodonium salt may not be preferred as the aryliodonium salt may interfer with the initiator system according to the present invention.

The term "electron donor" as used herein means a compound which is capable of donating electrons in a photochemical process. Suitable examples include organic compounds having heteroatoms with electron lone pairs, for example amine compounds. Preferred electron donors are based on Ge, Si and Sn. Ge and Si are more preferred.

The present invention relates to a dental composition. The dental composition may be a dental adhesive composition, a dental composite composition, a resin modified dental cement, a pit and fissure sealant, a desensitizer and a protective varnish. The dental composition may be cured by irradiation of actinic radiation.

The dental composition comprises one or more compounds having at least one polymerizable double bond. The one or more compounds having a polymerizable double bond may preferably be polymerizable N-substituted alkyl acrylic or acrylic acid amide monomers or a (meth)acrylate compounds.

A polymerizable N-substituted alkyl acrylic or acrylic acid amide monomer may be preferably selected from compounds characterized by one of the following formulas:

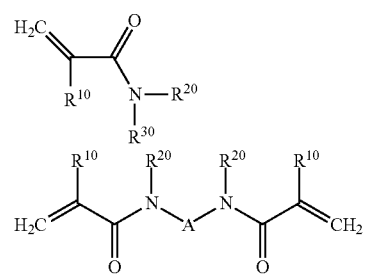

-continued $$\left[ H_2C \underset{\underset{O}{\|}}{\overset{R^{10}}{=}} \underset{}{\overset{R^{20}}{\underset{}{\text{N}}}} \right]_n Z$$

wherein $R^{10}$, $R^{20}$ and $R^{30}$ independently represent a hydrogen atom or a C1 to C8 alkyl group; A represents a divalent substituted or unsubstituted organic residue having from 1 to 10 carbon atoms, whereby said organic residue may contain from 1 to 3 oxygen and/or nitrogen atoms; Z represents a saturated at least trivalent substituted or unsubstituted C1 to C8 hydrocarbon group, a saturated at least trivalent substituted or unsubstituted cyclic C3 to C8 hydrocarbon group, and n is at least 3. Preferably, the one or more compounds having a polymerizable double bond include bisacrylamides such as N,N'-diethyl-1,3-bisacrylamido-propan (BADEP), 1,3-bisacrylamido-propan (BAP), 1,3-bisacrylamido-2-ethyl-propan (BAPEN), N,N'-(2E)-2-butene-1,4-diylbis[N-2-propen-1-yl-2-propenamide] (BAABE), N,N-di(cyclopropyl acrylamido) propane (BCPBAP) and N,N'-(2-hydroxy-1,3-propanediyl)bis[N-2-propen-1-yl-2-propenamide] (DAAHP).

A (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trihexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4 (2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Preferably, the one or more compounds having a polymerizable double bond each contain one or two radical-polymerizable groups.

It is preferable that a blending ratio of the one or more compounds having a polymerizable double bond to the entire dental composition is 5 to 80% by weight. More preferably, the blending ratio is 10 to 60% by weight.

According to a preferred embodiment, the dental composition of the present invention comprises a radical-polymerizable monomer having an acidic group.

The dental composition further comprises a polymerization initiator system.

The polymerization initiator system comprises a sensitizer. The sensitizer may be a single compound or a combination of two or more compounds. The sensitizer may be selected from a Norrish type I sensitizer and a Norrish type II sensitizer. The sensitizer may be selected from a 1,2-diketone, a 1,3 diketone, a phosphine oxide, an iodonium salt, a sulfonium salt, a phosphonium salt, or a pyridinium salt.

According to a preferred embodiment, a combination of a Norrish type I sensitizer and a Norrish type II is used as the sensitizer. Specifically, according to a preferred embodiment, the sensitizer is a combination of
(b1-a) a first sensitizer selected from an 1,2-diketone, and
(b1-b) a second sensitizer selected from iodonium salts.
Examples of suitable 1,2-diketones are camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Camphorquinone is preferred as a first sensitizer in combination with a iodonium salt as a second sensitizer.

Examples of suitable 1,3-diketones are dibenzoyl methane, benzoyl acetone and acetyl propionyl methane.

Examples of suitable phosphine oxide photoinitiators include 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X).

Examples of iodonium salts are represented by the following formula (VI):

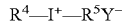 (III)

wherein $R^4$ and $R^5$
which are independent from each other represent an organic moiety, and
$Y^-$ is an anion.

Preferably, $R^4$ and $R^5$ represent an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, the iodonium salt is a diaryl iodonium salt. Examples of useful diaryl iodonium salt include (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium tetrafluoroborate, di(4-methylphenyl)iodonium tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, diphenyliodonium hexafluorophosphate, di(4-methylphenyl)iodonium hexafluorophosphate; diphenyliodonium hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, diphenyliodonium hexafluoroantimonate, 2,2'-diphenyliodonium tetrafluoroborate, di(2,4-dichlorophenyl) iodonium hexafluorophosphate, di(4-bromophenyl) iodonium hexafluorophosphate, di(4-methoxyphenyl) iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and diphenyliodonium hexafluoroantimonate.

Of the aromatic iodonium complex salts which are suitable for use in the compositions of the invention, include diaryliodonium hexafluorophosphate, diaryliodonium hexafluoroantimonate, (4-methylphenyl)[4-(2-methylpropyl) phenyl] iodonium hexafluoroantimonate, include (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-(1-methylethyl) phenyl 4-methylphenyliodonium tetrakis(pentafluorophenyl)borate.

Examples of iodonium, sulfonium or phosphonium salt respectively have the following formula:

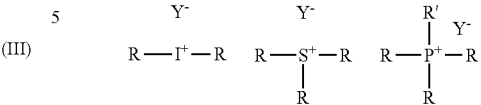

wherein the R which may be the same or different represent an aryl group which may be substituted, R' represents a hydrocarbon group and $Y^-$ is an anion selected from hexafluoroantimonate, trifluoromethylsulfate, hexafluorophosphate, tetrafluoroborate, hexafluoroarsenate, and tetraphenylborate. In the iodonium-, sulfonium or phosphonium salt, R is preferably a phenyl group which may be substituted with 1 to 3 substituents selected from halogen atoms, a cyano group, a hydroxy group, an amino group, $C_{1-6}$ alkyl groups and $C_{1-6}$ alkoxy groups. Preferably, R' is a linear, branched or cyclic alkyl group having 1 to 6 carbon atoms, which may be substituted with 1 to 3 groups selected from halogen atoms, a cyano group, a hydroxy group, an amino group, $C_{1-6}$ alkyl groups and $C_{1-6}$ alkoxy groups.

Preferably, the Norrish type I sensitizer is an organic phosphine oxide selected from the group consisting of 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X). More preferably, the Norrish type II sensitizer is 2,4-6-trimethylbenzoyl-diphenylphosphine oxide (Irgacure® TPO).

A Norrish type II sensitizer provides free radical intermediates by the photochemical abstraction. Typical Norrish type II sensitizer are e.g a 1,2-diketone, a 1,3 diketone.

In particular, the sensitizer (b1) is selected from camphor quinone and 2,4-6-trimethylbenzoyl-diphenylphosphine oxide (Irgacure® TPO).

When camphor quinone is selected as a first sensitizer (b1-a) which is of Norrish type II, then preferably, a second sensitizer (b1-b) which is of Norrish type I is present which is an iodonium salt.

The use of sensitizer (b1), in particular camphorquinone, together with an iodonium-, sulfonium or phosphonium salt may provide for a synergistic effect, in particular in the case of iodonium salts. Preferred iodonium salts are diphenyliodonium hexafluorophosphate, and (4-methylphenyl)[4-(2-methylpropyl)phenyl]iodonium hexafluorophosphate (Irgacure® 250, commercial product available from BASF SE). However, in case of a substituted aromatic tertiary phosphine compound, the presence of an aryliodonium salt may not be preferred as the aryliodonium salt may interfer with the initiator according to the present invention.

The polymerization initiator system further comprises an aromatic tertiary phosphine compound of formula (I). In the aromatic tertiary phosphine compound of the formula (I), moieties Z, $R^1$, Ar, R, L, Z, Z' may be defined as follows:

For $R^1$, the monovalent hydrocarbyl group may be an alkyl group, a cycloalkyl group, a cycloalkylalkyl group, an arylalkyl group or an aryl group.

Ar represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

L is a substituted or unsubstituted divalent hydrocarbyl group which may contain a linkage selected from an ether linkage, a thioether linkage, an ester linkage, an amide linkage, and a urethane linkage. For L, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and"-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl(diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl(diyl), cyclobutyl(diyl), cyclopentyl(diyl) and cyclohexyl(diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy(diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (I), any of the hydrocarbyl group may be substituted by on or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

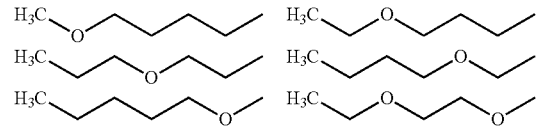

In formula (I), group $R^1$ and/or Ar as well as R and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^1$ and Ar independently are aromatic hydrocarbyl groups selected from a phenyl group, a naphtyl group, a tolyl group, a xylyl group, and a styryl group.

As regards R, this moiety is an aryl group, which may be substituted by one or more groups selected from a hydroxyl group, an amino group, a —$NR^2R^3$ group (wherein $R^2$ and $R^3$, which may be the same or different, are selected from $C_{1-6}$ alkyl groups), a carboxyl group, and a group having a polymerizable double bond. According to a preferred embodiment, R is an aryl group substituted by one or more groups selected from a hydroxyl group, an amino group, a —$NR^2R^3$ group (wherein $R^2$ and $R^3$, which may be the same or different, are selected from $C_{1-6}$ alkyl groups), a carboxyl group, and a group having a polymerizable double bond.

More preferably, R is a phenyl group substituted by one or two groups selected from a hydroxyl group, an amino group, a —$NR^2R^3$ group (wherein $R^2$ and $R^3$, which may be the same or different, are selected from $C_{1-6}$ alkyl groups), a carboxyl group, and a group having a polymerizable double bond.

Even more preferably, the aromatic phosphine compound is a compound of formula (I) wherein Z is a group of the following formula (III):

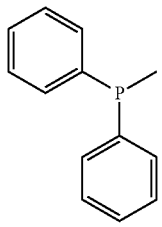

Specific examples for a compound of formula (I) include triphenyl phosphine (TPP), 4-(diphenylphosphino)styrene (DPPS), 4-(diphenylphosphino)benzoic acid, 4-(diphenylphosphino) benzoic acid, 3-(diphenylphophonino)propionic acid, (4-(diphenylphosphino) N,N"-dimethylaniline, 2,2'-bis(diphenylphosphino)benzophenone (BDPPEP), bis[2-(diphenylphosphino)phenyl]ether (BDPPE), (4-Hydroxyphenyl)diphenylphosphine, allyldiphenylphosphine. Preferably, the compound of formula (I) is triphenyl phosphine (TPP) or 4-(diphenylphosphino)styrene (DPPS), more preferably 4-(diphenylphosphino)styrene (DPPS).

It was surprisingly found that aromatic tertiary phosphine compounds of formula (I) provide for both an advantageous efficiency in terms of a higher polymerisation rate and a higher final conversion rate compared to a dental composition comprising a polymerization initiator system without an aromatic tertiary phosphine compound of formula (I). Advantageously, the polymeriation rate may be adjusted within a range which still provides for corrections when applying the dental composition to a patient's tooth or when forming a prosthesis. Although photopolymerization is achieved at a higher polymerisation and conversion rate, owing to the present polymerization initiator system, undesired side reaction resulting e.g. in discoloration of the cured dental composition can be effectively suppressed. Besides, by adding an aromatic tertiary phosphine compound of formula (I) to the present polymerization initiator system, a yellow coloration of the dental composition eventually formed already before light curing can efficiently be reduced/decreased. That is, there is a photo-bleaching effect which provides for an advantageous effective reduction/decrease of yellow discolorations of the dental composition, while the initiator system furthermore provides for an advantageous polymerization and conversation rate throughout the whole course of time of the photopolymerization.

The present polymerisation initiator system is not only advantageous for relatively thin films of up to 0.1 mm such as adhesive films, but also particularly suitable for polymerizing relative thick samples of a dental composition having a thickness of about 1 to 2 mm or more, such as fillings and prosthetics.

Without wishing to be bound to theory, it is believed that a synergistic effect due to the combination of (b1) the sensitizer and (b2) the aromatic tertiary phosphine of formula (I) is provided according to the present invention. The synergistic effect can be obtained with different types of sensitizers including type II sensitizers such as camphorquinoneand type I sensitizers such as the 2,4,6-trimethylbenzoyldiphenylphosphine oxide (Irgacure® TPO).

A further positive effect associated with the application of tertiary phosphines of formula (I) as initiators is that the present compositions exhibit an advantageous storage stability, that is the composition keep the above characteristics of an advantageous efficiency in terms of a higher polymerisation rate and a higher final conversion rate even after a long storage time, e.g. about 2 month.

From the above listed aromatic tertiary compounds of formula (I), 4-(diphenylphosphino)styrene (DPPS) is particularly preferred, since this compound provides for particularly improved photo-bleaching results compared to the already advantageous results obtained with triphenyl phosphine (TPP). Besides, DPPS is particularly suitable for initiating polymerization of thick samples of about 1 to 2 mm thickness. DPPS not only provides for an improved conversion rate, but with DPPS, the conversion rate of the dental composition can be maintained even after a storage time of 2 weeks or more.

A compound of the formula (I) may be a known compound which is commercially available or may be prepared according to published procedures. For example, a compound of formula (I) may be prepared via nickel-catalyzed cross-coupling of an aryl triflate or halide with chlorodiphenylphosphine in the presence of a $NiCl_2$(1,2-bis(diphenylphosphino)ethane) catalyst and elemental zinc (S. A. Laneman et al, *Chem. Commun.* 1997, 2359-2360):

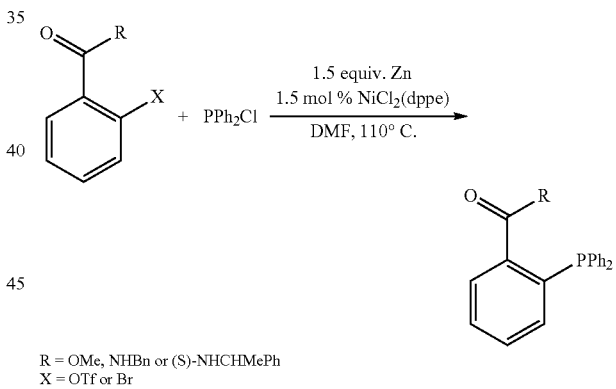

R = OMe, NHBn or (S)-NHCHMePh
X = OTf or Br

Alternatively, the compound of formula (I) may be prepared by coupling of an aryl halide to a diaryl- or dialkyl phosphine in the presence of a copper (I) salt catalyst and $K_2CO_3$ or $Cs_2CO_3$ as a base (S. L. Buchwald, *Org. Lett.* 2003, 5, 2315-1318; D. Van Allen, *J. Org. Chem.* 2003, 68, p. 4590-4593):

-continued

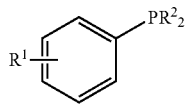

$R^1$ = 2-MeO, 2-NH$_2$, 4-CO$_2$Me, 2-Ph, 4-NH$_2$, 4-CO$_2$Et, 4-CN
X = I or Br
$R^2$ = Ph, Tol, Cy, iBu

A further alternative for preparing a compound of formula (I) is to a palladium-catalyzed phosphination of aryl bromides and triflates with triarylphospines, which has the advantage that it is compatible with several functional groups such as ketones, aldehydes, esters, nitriles, ethers (F. Y. Wong et al. in: Chem. Commun. 2000, p. 1069-1070; Tetrahedron Lett. 2000, 41, p. 10285-10289; Tetrahedron 2003, 59, p. 10295-10305; Tetrahedron 2004, 60, p. 5635-5645).

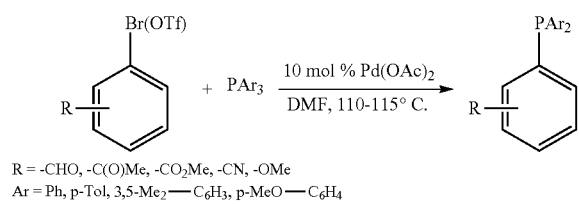

R = -CHO, -C(O)Me, -CO$_2$Me, -CN, -OMe
Ar = Ph, p-Tol, 3,5-Me$_2$—C$_6$H$_3$, p-MeO—C$_6$H$_4$

Preferably, the polymerization initiator system of the dental composition further comprises (b3) an electron-donor. Preferred electron-donors include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid or a coinitiator compound of the following formula (IV):

L-H     (IV)

wherein L is a moiety of the following formula (V)

$R^aR^bR^cX$—     (V)

wherein
X represents Si, Ge, or Sn and
$R^a$ represents a hydrogen atom, an organic moiety or a different moiety L;
$R^b$ and $R^c$
which are independent from each other, represent an organic moiety.

The coinitiator compound is a metal hydride. The metal hydride of formula (IV) may react as a hydrogen donating agent in a photoexcitation complex with the alpha-diketone sensitizer. Accordingly, when alpha-diketone absorbs visible light and forms an exciplex with the metal hydride of formula (IV), a hydrogen transfer may take place from the metal hydride to the alpha-diketone compound whereby the coinitiator of is transformed into a radical specifies capable of facilitating the polymerization reaction.

In formula (IV), L is a moiety of the following formula (V)

$R^aR^bR^cX$—     (V)

In formula (V), X represents Si, Ge, or Sn. Preferably, X represents Si or Ge. More preferably, X is Ge. According to a specific embodiment, the coinitiator compound is a silane compound. According to a further specific embodiment, the coinitiator compound is a germane compound.

In formula (V), $R^a$ may be a hydrogen atom, an organic moiety or a different moiety L. When $R^a$ is a hydrogen atom, then the coinitiator compound contains two metal hydride bonds (X—H). In case $R^a$ is a hydrogen atom, the X is Si.

When $R^a$ is an organic moiety, $R^a$ is preferably an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

When $R^a$ is a different moiety L, the coinitiator compound of the formula (IV) contains a metal-metal bond. In case two moieties A are present, then each X, $R^a$, $R^b$ and $R^c$ may be the same or different and independently has the meaning as defined by the present invention.

$R^b$ and $R^c$ which are independent from each other, represent an organic moiety. An organic group may be an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, $R^a$, $R^b$, and $R^c$ in the coinitiator compound of formula (IV) are the same and represent an aliphatic, an aromatic or an alicyclic hydrocarbon group.

According to a preferred embodiment, the coinitiator compound of formula (IV) is a compound of the following formula:

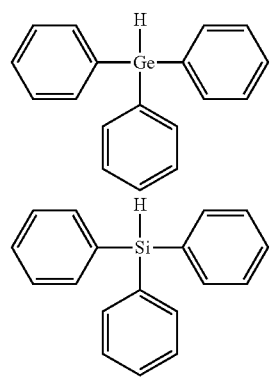

-continued

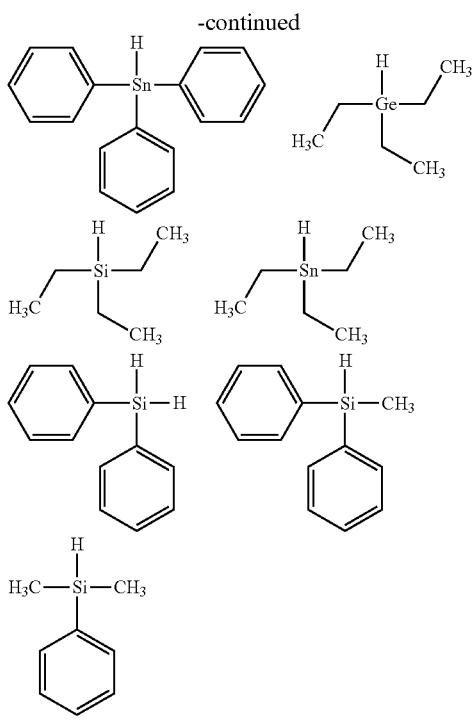

According to a preferred embodiment, the polymerizable matrix contains the coinitiator compound in an amount from 0.05 to 5 percent by weight based on the total weight of the composition.

Particularly preferred donors contain an electron donor atom such as a nitrogen, oxygen, phosphorus, or sulfur atom, and an abstractable hydrogen atom bonded to a carbon or silicon atom alpha to the electron donor atom.

More preferably, the electron-donor is an amine compound, even more preferably a tertiary amine selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. In particular, the tertiary amine is selected from the group consisting of triethanolamine, methyl 4-N, N-dimethylaminobenzoate, ethyl 4-N,N-dimethylaminobenzoate, 4-N,N-dimethylaminoethyl methacrylate and isoamyl 4-N,N-dimethylaminobenzoate.

In addition to these reducing materials, an organic metal compound, or a sulfinic acid derivative, can be used as a reducing material.

Preferably, in the present dental composition wherein the polymerization initiator system comprises component (b1), (b2), and (b3), the molar ratio ((b1):(b2):(b3)) is 1:(0.1 to 10.0):(0.0 to 5.0), more preferably 1:(0.1 to 6.5):(0.0 to 4.0), even more preferably 1:(0.1 to 3.0):(0.0 to 3.0). On the one hand, when the amount of the aromatic tertiary phosphine (b2) is below the above indicated lower limit of 0.1, then the conversion rate of the compounds having a polymerizable double bond, and the reaction rate of the polymerization reaction (in the following termed "polymerization rate") may be low. By means of the addition of the optional electron-donor (b3), both conversion rate and polymerization rate can be further advantageously adjusted.

Optionally, the dental compositions of the present invention may further comprise a solvent and/or a particulate filler.

Suitable solvents may be selected from water, alcohols such as methanol, ethanol, propanol (n-, i-), butanol (n-, iso-, tert.-), ketones such as acetone or the like.

The dental composition of the present invention may preferably comprise 5 to 75 percent by weight based on the total weight of the composition of a solvent.

Suitable particulate fillers may be selected from fillers currently used in dental compositions. The filler should be finely divided and preferably has a maximum particle diameter less than about 100 µm and an average particle diameter less than about 10 µm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental compositions of the present invention may further contain stabilizers, pigments, free radical scavengers, polymerization inhibitors, reactive and nonreactive diluents, coupling agents to enhance reactivity of fillers, rheology modifiers, and surfactants.

Suitable stabilizers may be selected from reducing agents such as vitamin C, inorganic sulfides and polysulfides and the like.

According to a further aspect of the invention, the aromatic phosphine compound of formula (I) is used for the preparation of a dental composition, more preferably the aromatic phosphine compound of formula (I) is 4-(diphenylphosphino)-styrene (DPPS). Accordingly, improved photo-bleaching results compared to the already advantageous results obtained with triphenyl phosphine (TPP) are obtained. Furthermore, DPPS is particularly suitable for initiating polymerization of thick samples of about 1 to 2 mm thickness. Besides, DPPS not only provides for an improved conversion rate, but with DPPS, the conversion rate of the dental composition can be maintained even after a storage time of 2 month or more.

According to a particularly preferred embodiment, the dental composition according to the invention comprises
(a) one or more compounds having at least one polymerizable double bond, preferably at least one of said compounds is selected from the group consisting of bis-GMA/TGDMA, UDMA, PENTA and BADEP;
(b) a polymerization initiator system comprising
(b1) a sensitizer selected from camphor quinone (CQ) and 2,4-6-trimethylbenzoyl-diphenylphosphine oxide (Irgacure® TPO); and
(b2) an aromatic tertiary phosphine compound of formula (I) selected from the group consisting of triphenyl phosphine (TPP), 4-(diphenylphosphino)styrene (DPPS), 4-(diphenylphosphino)benzoic acid, 4-(diphenylphosphino) benzoic acid, 3-(diphenylphophonino)propionic acid, (4-(diphenylphosphino) N,N'-dimethylaniline, 2,2"-bis(diphenylphosphino) benzophenone (BDPPEP), bis[2-(diphenylphosphino)phenyl]ether (BDPPE), (4-hydroxyphenyl)diphenylphosphine, allyldiphenylphosphine; preferably, the compound of formula (I) is triphenyl phosphine (TPP) and/or 4-(diphenylphosphino)styrene (DPPS), more preferably 4-(diphenylphosphino)styrene (DPPS); and
(b3) optionally at least one electron-donor in the form of an amine compound, preferably a tertiary amine selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate, isoamyl 4-N,N-dimethylaminobenzoate, N,N-dimethylaniline, N,N-dimethyltoluidine, N,N-diethanoltoluidine, dimethylaminoanisole and 1 or 2-dimethylaminonaphthalene;
more preferably, the tertiary amine is selected from the group consisting of triethanolamine, methyl 4-N,N-dimethylaminobenzoate, ethyl 4-N,N-dinnethylaminobenzoate (EDB), 4-N,N-dimethylaminoethyl methacrylate and isoamyl 4-N,N-dinnethylaminobenzoate;
even more preferably, the tertiary amine is EDB, wherein the polymerization initiator system comprises component (b1), (b2) and (b3) preferably in a molar ratio of 1:(0.1 to 3.0):(0.0 to 3.0).

When camphor quinone is selected as a first sensitizer (b1-a) which is of Norrish type II, then preferably, a second sensitizer (b1-b) which is of Norrish type I is present which is an iodonium salt.

EXAMPLES

Materials

The investigated sensitizers: camphorquinone and 2,4,6-trimethylbenzoyldiphenylphosphine oxide (Irgacure® TPO) were obtained from Aldrich and BASF respectively and used as representative Type II and Type I sensitizers respectively (Scheme 1).

Triphenyl phosphine (TPP) and 4-(diphenylphosphino) styrene (DPPS) (from Aldrich) were used as aromatic tertiary phosphines (Scheme 1).

Ethyldimethylaminobenzoate (EDB) (from Lamberti Spa) was used as electron-donor.

Bisphenol A-glycidyl methacrylate (Bis-GMA) and triethyleneglycol dimethacrylate (TEGDMA) were obtained from Sigma-Aldrich and used with the highest purity available (Scheme 1). A blend Bis-GMA/TEGDMA (70%/30% w/w) was used as benchmark matrix for dental material photopolymerizations.

Scheme 1. Chemical structures of the photoinitiators, additives and monomers.

sensitizers:

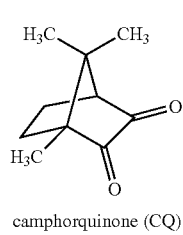

camphorquinone (CQ)

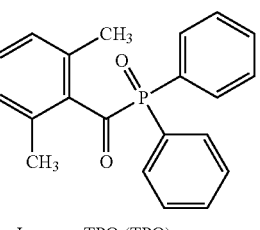

Irgacure TPO (TPO)

-continued aromatic teriary phosphine compound of formula (I):

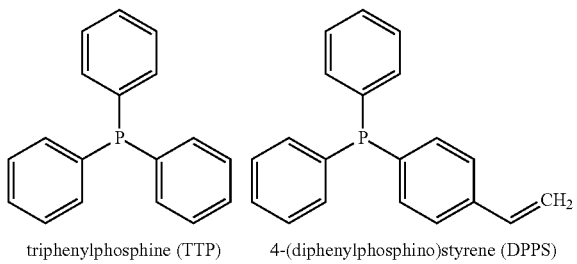

triphenylphosphine (TTP)   4-(diphenylphosphino)styrene (DPPS)

electron donor:

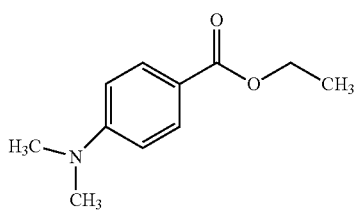

ethyldimethylaminobenzoate (EDB)

compounds having a polmyerizable double bond:

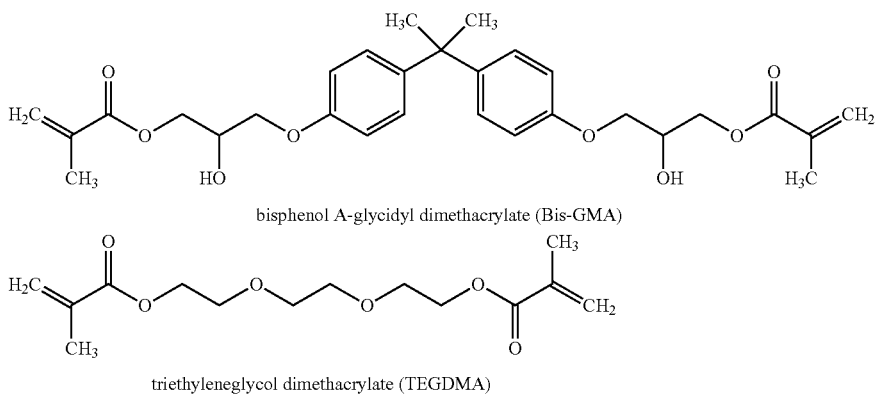

bisphenol A-glycidyl dimethacrylate (Bis-GMA)

triethyleneglycol dimethacrylate (TEGDMA)

Irradiation Sources

Figure 1B:
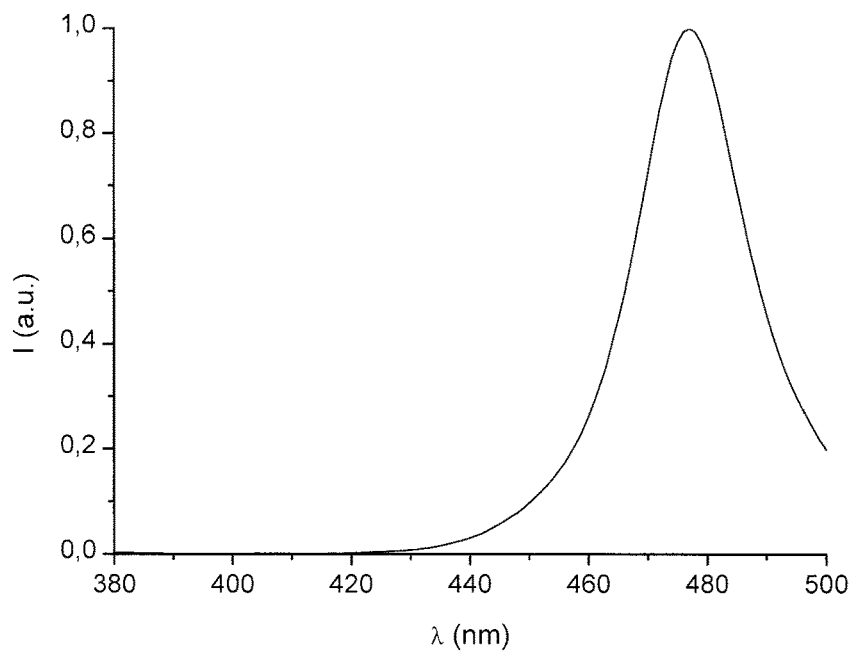

Several light sources were used for the irradiation of the photocurable samples: LED centered at 405 nm (M405L2—ThorLabs; about 1100 mW/cm$^2$) and blue dental LED centered at 477 nm (SmartLite® Focus from Dentsply, about 1000 mW/cm$^2$ in the selected conditions). The emission spectra of the irradiation sources are given in FIGS. 1a and 1b.

Steady State Photolysis Experiments

The studied formulations were irradiated with the SmartLite® Focus pen-style LED curing light from Dentsply, and the UV-vis spectra were recorded using an Ocean Optics spectrophotometer at different irradiation time. The white light has been provided by a cool white LED from Thorlab. In addition, color measurements have also been performed and pictures have been taken to illustrate the photo-bleaching on 1.4 mm thick samples.

Figure 2:
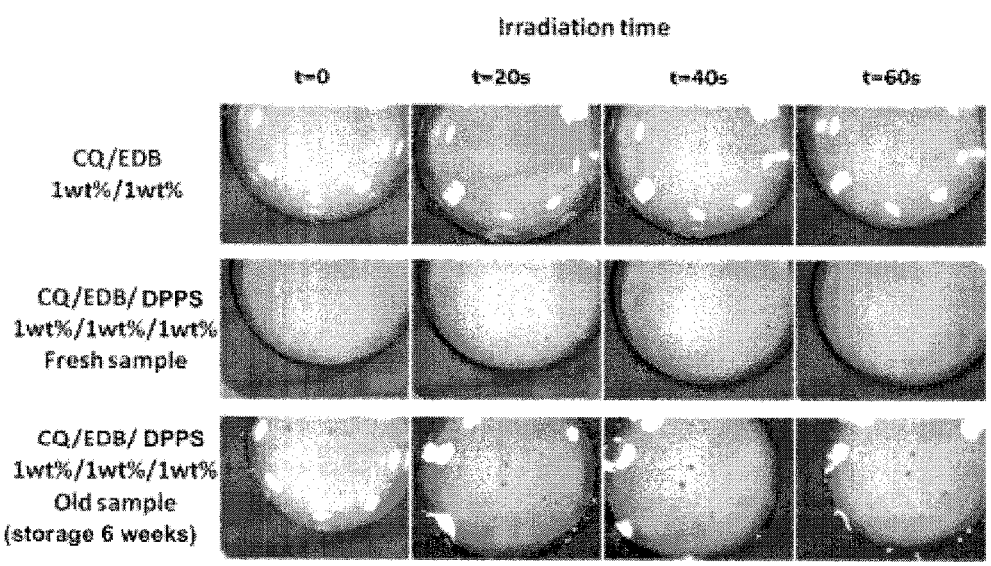
FIG. 2 is a picture of three bisphenol A-glycidyl methacrylate (Bis-GMA)/triethyleneglycol dimethacrylate (TEGDMA) (70%/30% w/w) formulations cured with a blue LED with different irradiation time. The "old" sample is a sample being 6 weeks old, the "fresh" sample is only half a day old.
Figure 3:
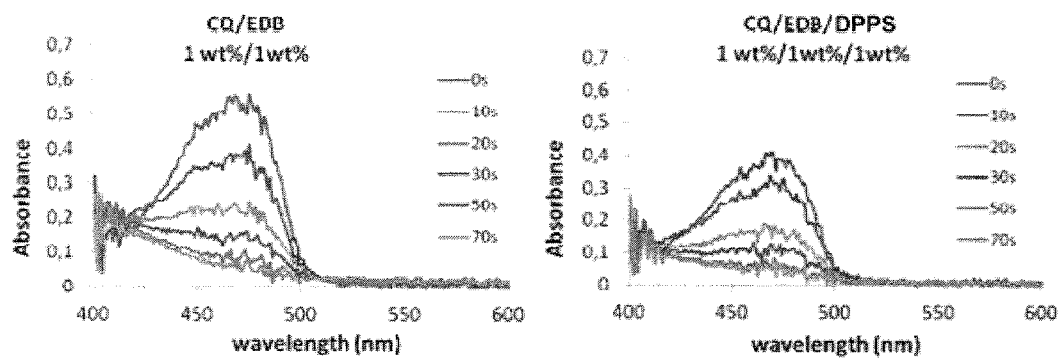
FIG. 3 shows diagrams of the photolysis of the formulations followed by visible spectroscopy for two Bis-GMA/TEGMA (70%/30% w/w) formulations with and without DPPS.
Figure 4:
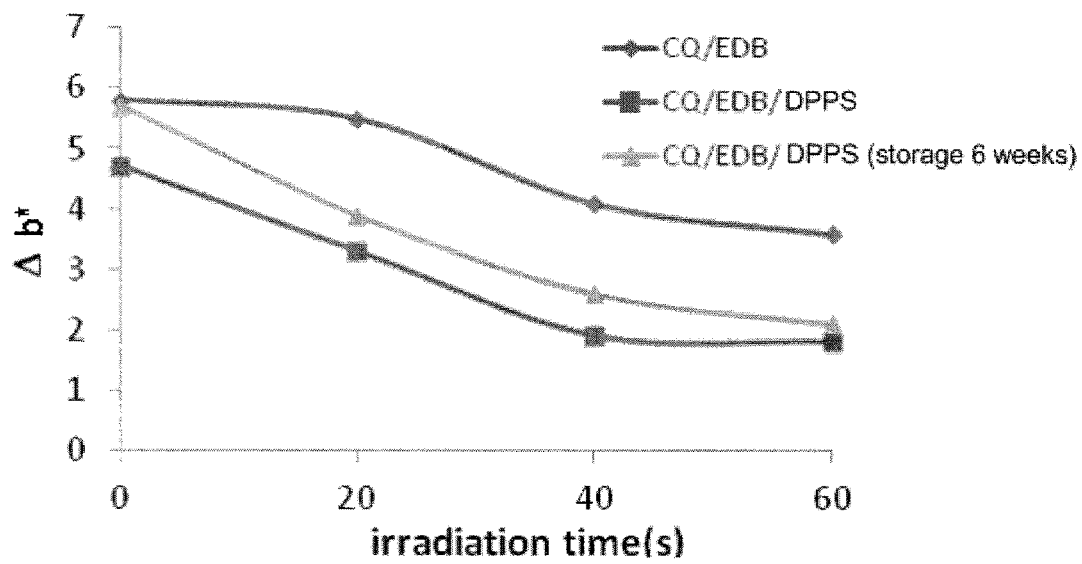
FIG. 4 shows the evolution of the yellowing during the irradiation for three formulations using the L*, a*, b* color space system.

All the results obtained in FIGS. 2, 3 and 4 show that the photo-bleaching of the formulations with and without DPPS are quite similar showing most of the time a lower yellowing after 60 s of irradiation with the blue LED. DPPS does therefore slightly improve the photo-bleaching of the formulation perhaps due to an increase of reactivity that consumes more camphorquinone for a same light dose.

Photopolymerization Experiments

For photopolymerization experiments, the conditions are given in the figure captions. The photosensitive formulations were deposited on a BaF$_2$ pellet under air (20 µm thick for adhesives and 1.4 mm for thick samples) for irradiation with different lights. The evolution of the double bond content of methacrylate was continuously followed by real time FTIR spectroscopy (JASCO FTIR 4100)[29,30] at about 1630 cm$^{-1}$ for thin samples (10-25 µm) or 6165 cm$^{-1}$ for thick samples (1-2 mm—use of NIR), respectively.

Figure 5A:
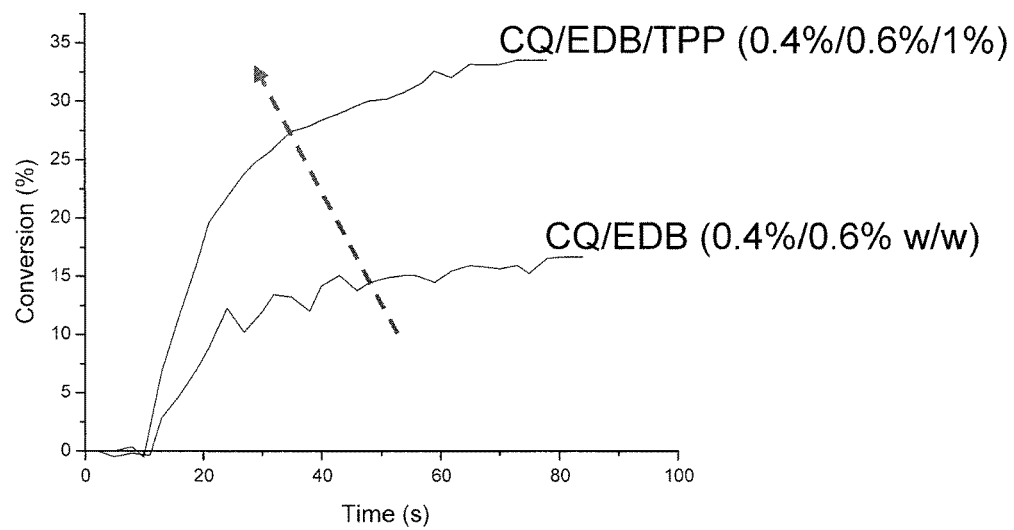
FIGS. 5a, 5b and 5c respectively show the polymerization profiles of a dental resin under air upon a SmartLite® Focus exposure for the following different initiating systems.
Figure 5B:
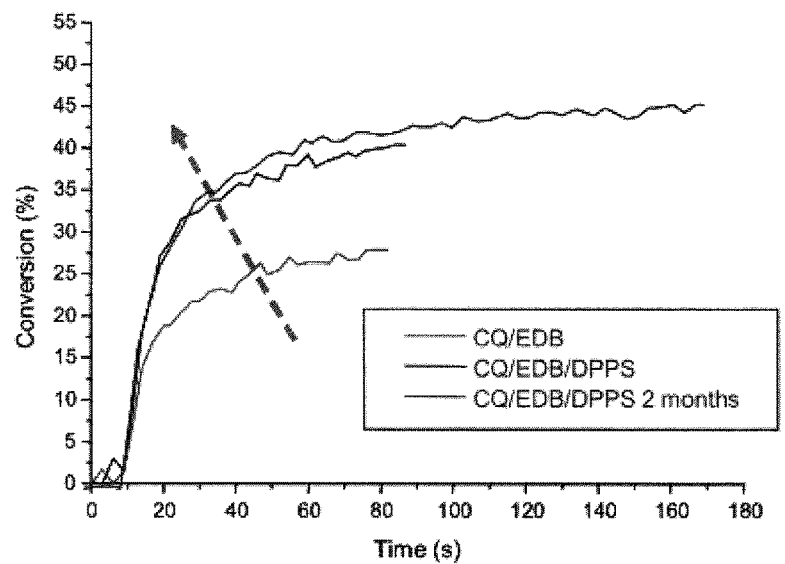
Figure 5C:
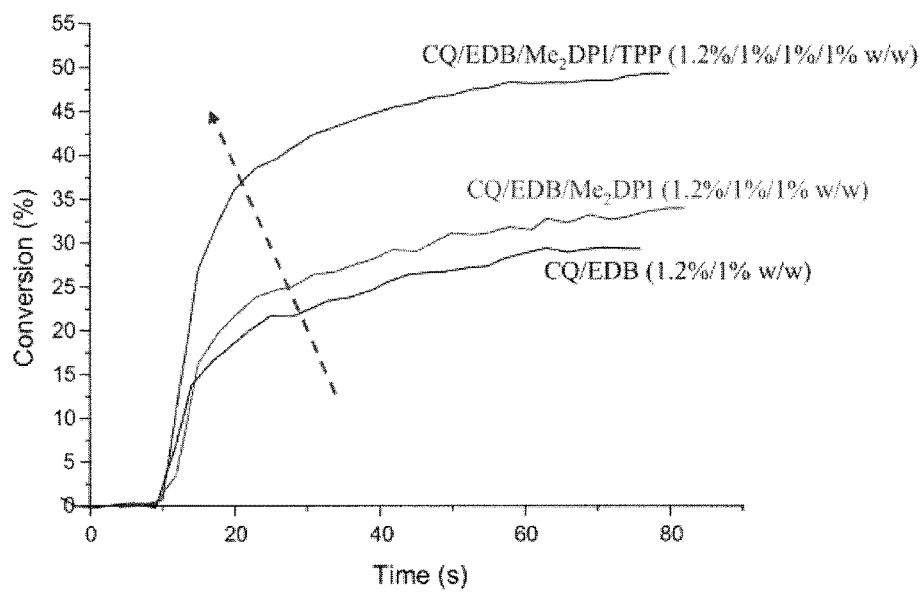

Results:

1. CQ/EDB/TPP or CQ/EDB/DPPS as Polymerization Initiator Systems for Adhesives:

The CQ/EDB system exhibits a good efficiency upon blue LED irradiation (FIG. 5a, 5b). The final conversion is 60% for polymerization in laminate, i.e. when the dental composition is covered with means for separating it from the air atmosphere, i.e. a translucent foil, but only about 28% for polymerization under air (FIG. 5a). In the presence of TPP or DPPS, a better efficiency is found with higher final conversion (FIGS. 5a, 5b and Table 1). Interestingly, the formulations in the presence of DPPS are very stable as similar polymerization profiles are found for fresh sample and after 2 months of storage at room temperature (FIG. 5b). TPP and DPPS can also be used as aromatic tertiary phosphines for a three-component system CQ/EDB/Diphenyliodonium hexafluorophosphate (Table 1; FIG. 5b).

TABLE 1

Final conversion (FC) (% for 70 s of irradiation) for the polymerization of a blend Bis-GMA/TEGDMA (70%/30% w/w); SmartLite ® Focus irradiation.

| Photoinitiating system | FC (%) Under Air | FC (%) laminate |
|---|---|---|
| CQ/EDB (0.4%/0.6% w/w) | 17 | |
| CQ/EDB/TPP (0.4%/0.6%/1% w/w) | 35 | |
| CQ/EDB/DPI (1.2/1/1% w/w) | 32 | |
| CQ/EDB/DPI/TPP (1.2/1/1/1% w/w) | 50 | |
| CQ/EDB (1%/1% w/w) | 28 | 60 |
| CQ/EDB/DPPS (1%/1%/1% w/w) | 40 (42[a]) | 61 |

[a] after 2 months of storage at RT.

Figure 6:
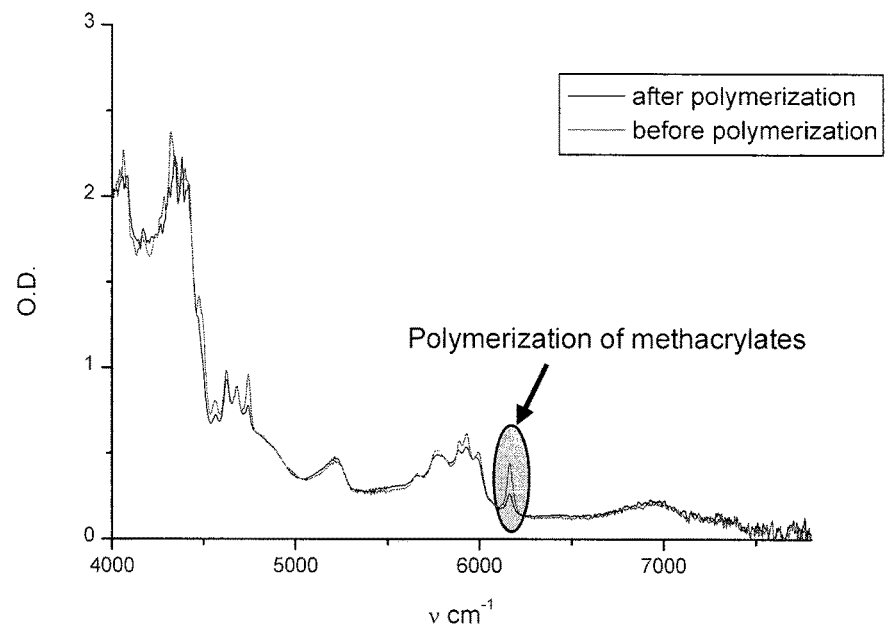
FIG. 6 shows a FTIR spectra before and after polymerisation of a dental resin under air upon a "SmartLite® Focus" exposure; initiating system: CQ/EDB/DPPS 1%/1%/1% w/w.
Figure 7:
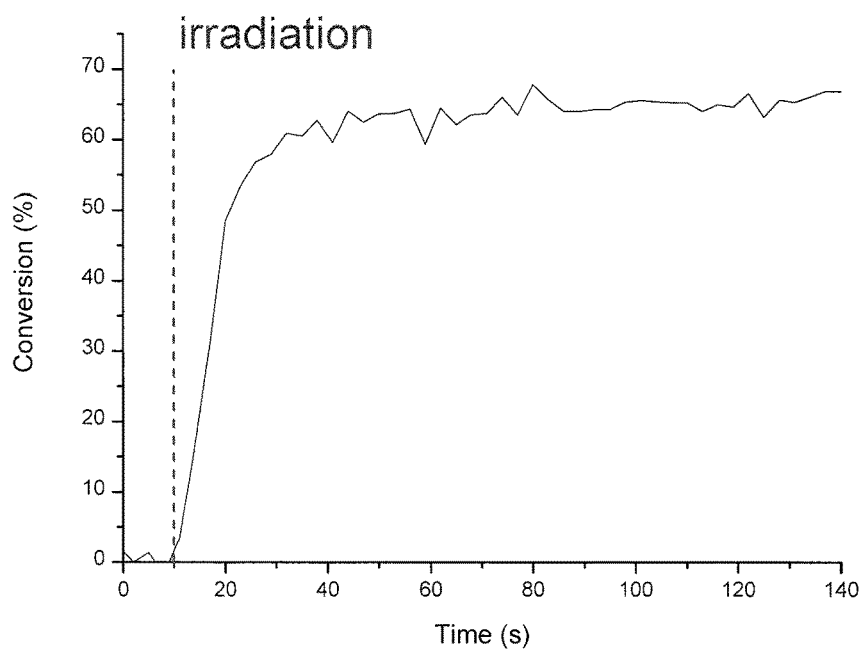
FIG. 7 shows polymerization profiles of a dental resin under air upon a SmartLite® Focus for an initiating system CQ/EDB/DPPS 1%/1%/1% w/w.

The polymerization can be followed by near infrared irradiation (NIR) at 6165 cm$^{-1}$ (FIG. 6). The polymerization is very efficient with a final conversion of about 65% (FIG. 7).

Figure 8:
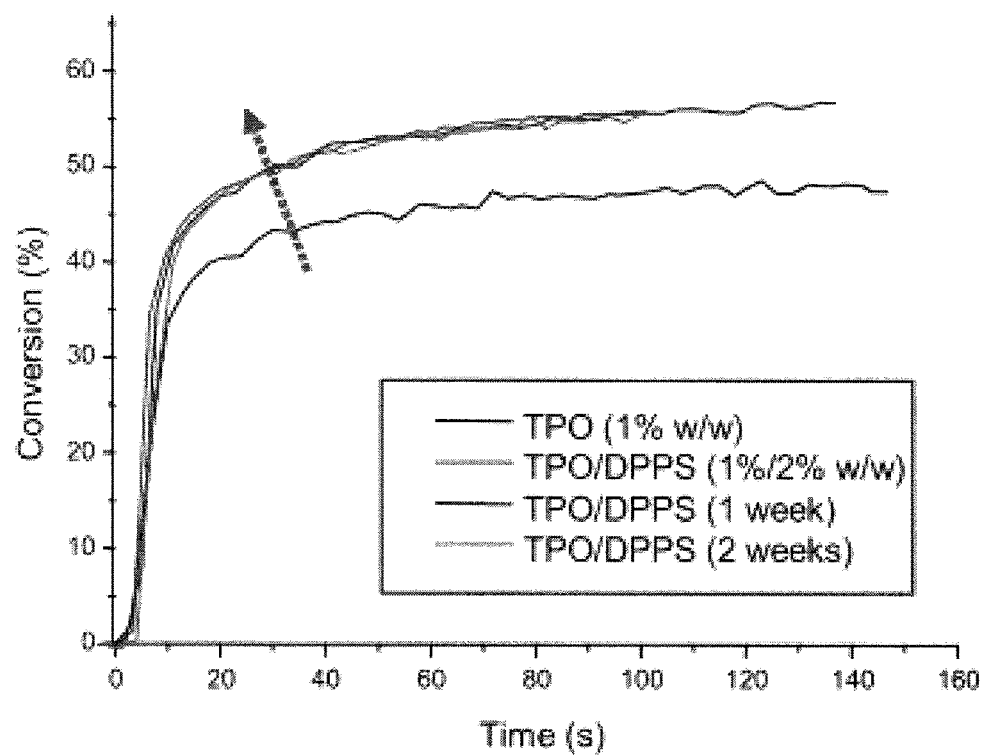
FIG. 8 shows polymerization profiles of a dental resin under air upon a LED©405 nm exposure for initiating systems Irgacure® TPO and Irgacure® TPO/DPPS. For Irgacure® TPO/DPPS, the polymerization profiles for different storage time at room temperature are also depicted.
Figure 9A:
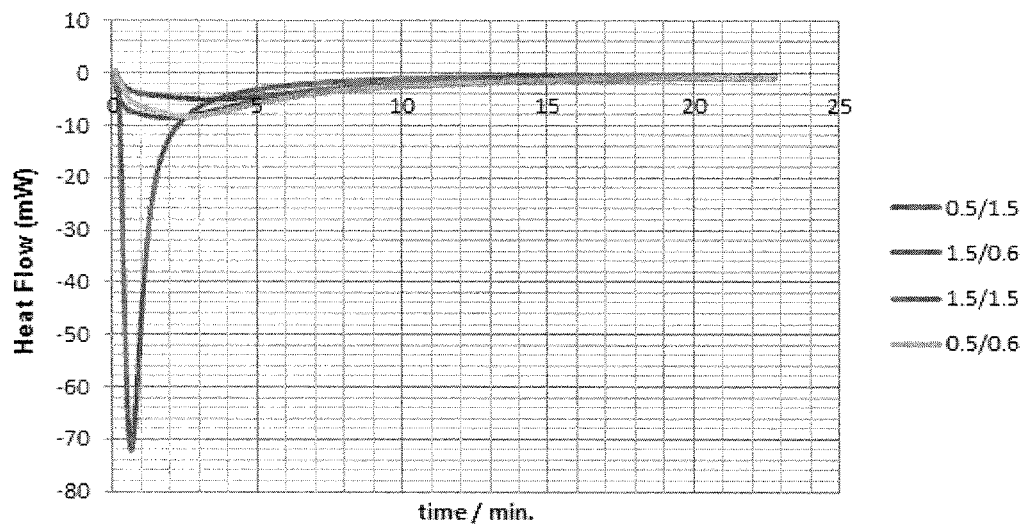
FIGS. 9a and 9b show diagrams of heat flow (mW) versus time (min) obtained by means of differential scanning calorimetry measurements.
Figure 9B:
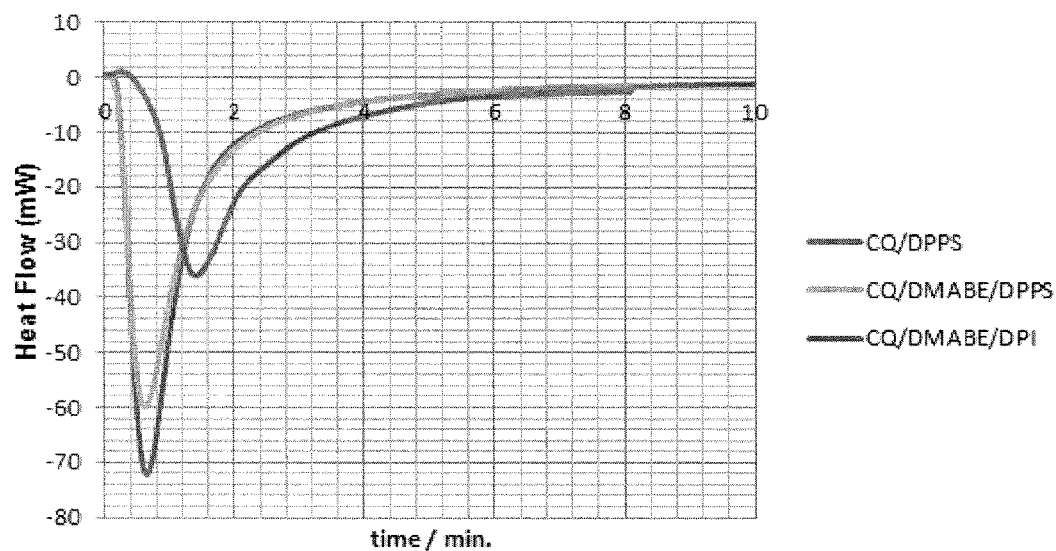
Figure 10:
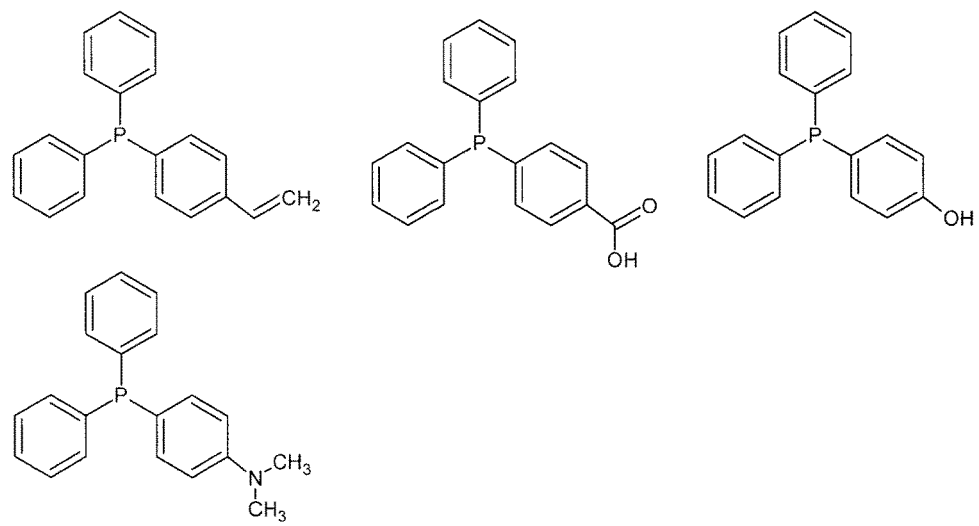
FIG. 10 shows structural formulae of preferred aromatic tertiary phosphines of formula (I).

2. DPPS as Aromatic Teriary Phosphine in Type I Photoinitiating System (Irgacure® TPO):

DPPS can also be used together with Type I sensitizers. An example is given in FIG. 8 for Irgacure® TPO upon a LED©405 nm exposure. For a dental resin, the final conversion increases from 47% in absence of DPPS to 57% in presence of DPPS (FIG. 8). The formulations in presence of DPPS are also very stable (similar polymerization profiles are obtained after 2 weeks of storage at room temperature—FIG. 8).

3. Measurement of Polymerization Enthalpy of the Polymerization Initiator System CQ/DMABE Optionally Additionally Comprising DPI and/or DPPS The compositions according to Examples 1 to 3 and Comparative Examples 1 to 4 have been prepared as described below, wherein the resulting compositions of the starting materials were polymerized at 37° C. Then, the polymerization enthalpies of these compositions were measured with the differential scanning calorimeter DSC 7 from Perkin Elmer. The results of these measurements are summarized in Table 2 below.

Example 1

5.0000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0232 g (0.1395 mmol) camphorquinone (CQ), 0.0323 g (0.1673 mmol) 4-(dimethylamino) benzoic acid ethylester (EDB), 0.0402 (0.1395 mmol) 4-(Diphenylphosphino) styrene and 0.0057 g (0.0260 mmol) 2,6-di-tert-butyl-p-cresol were mixed homogeneously.

Example 2

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0099 g (0.051 mmol) 4-(dimethylamino) benzoic acid ethylester (EDB), 0.0123 (0.0425 mmol) 4-(Diphenylphosphino) styrene and 0.0017 g (0.0079 mmol) 2,6-di-tert-butyl-p-cresol were mixed homogeneously.

Comparative Example 1

5.0000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0232 g (0.1395 mmol) camphorquinone (CQ), 0.0324 g (0.1674 mmol) 4-(dimethylamino) benzoic acid ethylester (EDB) and 0.0057 g (0.0260 mmol) 2,6-di-tert-butyl-p-cresol were mixed homogeneously.

Comparative Example 2

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0099 g (0.051 mmol) 4-(dimethylamino) benzoic acid ethylester (EDB) and 0.0017 g (0.0079 mmol) 2,6-di-tert-butyl-p-cresol were mixed homogeneously.

TABLE 2

Polymerization enthalpy[*] of the polymerization initiator systems comprising CQ/(EDB in combination with DPPS.

| Examples | Matrix | CQ [mol-%] | EDB [mol-%] | DPPS [mol-%] | $\Delta_R H$ [kJ/mol] |
|---|---|---|---|---|---|
| Example 1 | Bis-GMA/TGDMA | 0.9580 | 1.1489 | 0.9580 | −57.3 ± 0.4 |
| Comparative Example 1 | Bis-GMA/TGDMA | 0.9767 | 1.1720 | — | −52.4 ± 1.9 |
| Example 2 | UDMA | 0.9673 | 1.1600 | 0.9673 | −77.9 ± 7.0 |
| Comparative Example 2 | UDMA | 0.9767 | 1.1720 | — | −52.1 ± 1.5 |

[*] polymerisation was carried out at 37° C.

The polymerization enthalpy was measured at 37° C. polymerisation temperature, wherein $\Delta_R H$ for 100% conversion rate of the acrylate groups is about −80 kJ/mol. That is, in Example 2, almost full conversion of the compounds having a polymerizable double bond of the UDMA matrix is attained.

The DSC measurements show that the polymerization enthalpy of the DPPS based polymerization initiator systems (Example 1) are 11 or 12% higher compared to the CQ/amine system (Comparative Example 1) when bis-GMA/TGDMA is used as a model matrix. In UDMA the polymerization enthalpy of the DPPS based polymerization initiator system (Example 2) is even 32% higher compared to the CQ/EDB/DPI polymerization initiator system (Comparative Example 2).

4. Measurement of Polymerization Enthalpy and Kinetics of the Polymerization Initiator System Comprising CQ and Additionally DMABE and/or DPPS The compositions according to Examples 4 to 13 and Comparative Examples 5 and 6 have been prepared as described below, wherein the resulting compositions of the starting materials were polymerized at 37° C. Then, the polymerization enthalpies of these compositions were measured with the differential scanning calorimeter DSC 7 from Perkin Elmer. The results of these measurements are summarized in Table 3 below.

Example 4

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0212 g (0.1275 mmol) camphorquinone (CQ), 0.0368 (0.1275 mmol) 4-(Diphenylphosphino) styrene and 0.0017 g (0.0079 mmol) 2,6-di-tert-butyl-p-cresol were mixed homogeneously.

Example 5

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0147 (0.0510 mmol) 4-(Diphenylphosphino) styrene and 0.0017 g (0.0079 mmol) 2,6-di-tert-butyl-p-cresol were mixed homogeneously.

Example 6

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0099 g (0.051 mmol) 4-(dimethylamino) benzoic acid ethylester (EDB), 0.0123 (0.0425 mmol) 4-(Diphenylphosphino) styrene and 0.0017 g (0.0079 mmol) 2,6-di-tert-butyl-p-cresol were mixed homogeneously.

Example 7

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0141 g (0.0850 mmol) camphorquinone (CQ), 0.0099 g (0.051 mmol) 4-(dimethylamino) benzoic acid ethylester (EDB), 0.0245 (0.0850 mmol) 4-(Diphenylphosphino) styrene and 0.0017 g (0.0079 mmol) 2,6-di-tert-butyl-p-cresol were mixed homogeneously.

Example 8

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0212 g (0.1275 mmol) camphorquinone (CQ), 0.0368 (0.1275 mmol) 4-(Diphenylphosphino) styrene, 0.0099 g (0.051 mmol) 4-(dimethylamino) benzoic acid ethylester (EDB) and 0.0017 g (0.0079 mmol) 2,6-di-tert-butyl-p-cresol were mixed homogeneously.

Example 9

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0368 (0.1275 mmol) 4-(Diphenylphosphino) styrene, 0.0246 g (0.1275 mmol) 4-(dimethylamino) benzoic acid ethylester (EDB) and 0.0017 g (0.0079 mmol) 2,6-di-tert-butyl-p-cresol were mixed homogeneously.

Example 10

2.0000 g (4.2503 mmol) 11,14-Dioxa-2,9-diazaheptadec-16-enoicacid, 4,4,6,16 (or 4,6,6,16)-tetramethyl-10,15-dioxo-,2[(2-methyl-1-oxo-2-propen-1-yl)oxy]ethyl ester (UDMA), 0.0071 g (0.0425 mmol) camphorquinone (CQ), 0.0147 (0.0510 mmol) 4-(Diphenylphosphino) styrene, 0.0246 g (0.1275 mmol) 4-(dimethylamino) benzoic acid ethylester (EDB) and 0.0017 g (0.0079 mmol) 2,6-di-tert-butyl-p-cresol were mixed homogeneously. Polymerization enthalpy measured with the DSC 7 (Perkin Elmer) is summarized in Table 1.

Example 11

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0212 g (0.1275 mmol) camphorquinone (CQ), 0.0368 (0.1275 mmol) 4-(Diphenylphosphino) styrene, 0.0246 g (0.1275 mmol) 4-(dimethylamino) benzoic acid ethylester (EDB) and 0.0017 g (0.0079 mmol) 2,6-di-tert-butyl-p-cresol were mixed homogeneously.

Example 12

2.0000 g (4.2503 mmol) 11,14-Dioxa-2,9-diazaheptadec-16-enoicacid, 4,4,6,16 (or 4,6,6,16)-tetramethyl-10,15-dioxo-,2[(2-methyl-1-oxo-2-propen-1-yl)oxy]ethyl ester (UDMA), 0.0212 g (0.1275 mmol) camphorquinone (CQ), 0.0147 (0.0510 mmol) 4-(Diphenylphosphino) styrene, 0.0246 g (0.1275 mmol) 4-(dimethylamino) benzoic acid ethylester (EDB) and 0.0017 g (0.0079 mmol) 2,6-di-tert-butyl-p-cresol were mixed homogeneously.

Example 13

5.0000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0232 g (0.1395 mmol) camphorquinone (CQ), 0.0323 g (0.1673 mmol) 4-(dimethylamino) benzoic acid ethylester (EDB), 0.0402 (0.1395 mmol) 4-(Diphenylphosphino) styrene and 0.0057 g (0.0260 mmol) 2,6-di-tert-butyl-p-cresol were mixed homogeneously.

Comparative Example 5

2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 0.0071 g (0.0425 mmol) camphorquinone (CQ), 0.0099 g (0.051 mmol) 4-(dimethylamino) benzoic acid ethylester (EDB) and 0.0017 g (0.0079 mmol) 2,6-di-tert-butyl-p-cresol were mixed homogeneously.

Comparative Example 6

5.0000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0232 g (0.1395 mmol) camphorquinone (CQ), 0.0324 g (0.1674 mmol) 4-(dimethylamino) benzoic acid ethylester (EDB) and 0.0057 g (0.0260 mmol) 2,6-di-tert-butyl-p-cresol were mixed homogeneously.

TABLE 3

Polymerization enthalpy*) of the polymerization initiator systems comprising CQ in combination with EDB and/or DPPS.

| Examples | Matrix | CQ [mol-%] | EDB [mol-%] | DPPS [mol-%] | $\Delta_R H$ [kJ/mol] | $t_{hmax}$ [min] |
|---|---|---|---|---|---|---|
| Example 4 | UDMA | 2.8252 | — | 2.8252 | −61.2 ± 0.2 | 0.646 |
| Example 5 | UDMA | 0.9767 | — | 1.1720 | −52.8 ± 0.5 | 2.653 |
| Example 6 | UDMA | 0.9673 | 1.1600 | 0.9673 | −77.9 ± 7.0 | 0.632 |
| Example 7 | UDMA | 1.8978 | 1.1380 | 1.8978 | −57.0 ± 1.8 | 0.378 |
| Example 8 | UDMA | 2.7937 | 1.1168 | 2.7937 | −58.7 ± 0.9 | 0.314 |
| Example 9 | UDMA | 0.9330 | 2.7989 | 2.7989 | −56.3 ± 0.6 | 0.444 |
| Example 10 | UDMA | 0.9489 | 2.8467 | 1.1387 | −58.6 ± 2.0 | 0.375 |
| Example 11 | UDMA | 2.7476 | 2.7476 | 2.7476 | −61.9 ± 0.1 | 0.355 |

TABLE 3-continued

Polymerization enthalpy*⁾ of the polymerization initiator systems comprising CQ in combination with EDB and/or DPPS.

| Examples | Matrix | CQ [mol-%] | EDB [mol-%] | DPPS [mol-%] | $\Delta_R H$ [kJ/mol] | $t_{hmax}$ [min] |
|---|---|---|---|---|---|---|
| Example 12 | UDMA | 2.7936 | 2.7936 | 1.1175 | −60.6 ± 2.1 | 0.285 |
| Comparative Example 5 | UDMA | 0.9767 | 1.1720 | — | −52.1 ± 1.5 | 0.517 |
| Example 13 | Bis-GMA/ TGDMA | 0.9580 | 1.1489 | 0.9580 | −57.3 ± 0.4 | 0.553 |
| Comparative Example 6 | Bis-GMA/ TGDMA | 0.9767 | 1.1720 | — | −52.4 ± 1.9 | 0.592 |

*⁾polymerisation was carried out at 37° C.

The polymerization enthalpy was measured at 37° C. polymerisation temperature, wherein $\Delta_R H$ for 100% conversion rate of the acrylate groups is about −80 kJ/mol.

The DSC measurements show that the polymerization enthalpy of the DPPS based polymerization initiator systems (Examples 4 to 12) was 1.3 to 49.5% higher compared to the CQ/amine system (Comparative Example 5) if UDMA is used as a model matrix. In Example 6, the highest polymerization enthalpy of −77.9 kJ/mol was attained, that is almost 100% conversion of compound having a polymerizable double bond in the matrix system.

Furthermore, from the DSC results obtained for Examples 4 to 12 it can be gathered that the ratio between sensitizer CQ, aromatic compound DPPS and optional electron-donor EDB appears to be important. In Example 4 where a polymerisation initiator system comprising only the two components sensitizer CQ, aromatic tertiary amine compound DPPS, a remarkable improvement of 17.5% (compared with Comparative Example 5) was obtained when the molar ratio between CQ and DPPS was 1:1. By contrast, in Example 5 where also the aforementioned two component polymerization initiator system is applied, but the molar ratio between CQ and DPPS was 0.83, only a slight improvement of 1.34% is obtained compared with Comparative Example 5.

In the polymerization initiator system comprising the three components sensitizer CQ, aromatic tertiary phosphine compound DPPS and electron-donor EDB, an excellent improvement of 49.5% was obtained at a molar ratio of CQ:DPPS:EDB of 1:1.2:1. By contrast, only a slight improvement of 8.1% was obtained at a molar ratio of CQ:DPPS:EDB of 1:3:3. Besides, it appears to be advantageous to apply the polymerization initiator system in relatively small amounts compared to the matrix, what can be gathered from the comparison of Examples 6 and 11: in Example 6, the molar ratio CQ:DPPS:EDB is 1:1.2:1, wherein each component is contained in the matrix in an amount of about 1 mol %, while in Example 11, where the molar ratio is quite close to that of Example 6, namely CQ:DPPS:EDB is 1:1:1, each component is contained in the matrix in an amount of about 2 mol %. The result obtained in Example 11 is still good with an improvement of 18.8% compared with Comparative Example 5, however in Example 5, an even more significant improvement of 49.5% is obtained compared with Comparative Example 5.

In the bis-GMA/TGDMA matrix, the polymerization enthalpy of the DPPS based polymerization initiator system (Example 13) is 9.4 $ higher compared to the CQ/EDB polymerization initiator system (Comparative Example 6).

In Examples 4 to 13 and Comparative Examples 5 and 6, besides of the polymerisation enthalpy $\Delta_R H$, also the kinetics of the polymerization was measured by determining $t_{hmax}$, that is the time required for obtaining the indicated polymerization enthalpies. In Example 6, almost 100% conversion is attained, wherein $t_{hmax}$ is only slightly slower, namely about 22% compared to Comparative Example 5. A surprisingly rapid polymerization with $t_{hmax}$ being 45% less compared with Comparative Example 5 is obtained in Example 12, in which polymerization enthalpy and thus conversion rate is also advantageously 16% higher compared to Comparative Example 5.

In conclusion, the above experimental examples support that owing to the present polymerization initiator system, both a high conversion rate of the compounds having a polymerizable double bond of the matrix material and advantageous kinetics in terms of the polymerization time were obtained. From the above examples, it appears that these advantageous effects are attained due to synergistic effects between sensitizer, aromatic tertiary phosphine and optional electron donor of the present polymerisation initiator system.

Application Example 1: Dental Adhesive Composition—Release of DPPS

The sample is a mixture of the formulation A292 (description given in Table 2) and 1 wt % of DPPS. Photopolymerization was carried out for 40 s with the LED SmartLight® Focus (Dentsply). The 143 mg of dry photopolymer has been crushed and sonicated in 1.4 mL of acetonitrile. The immersion of the crushed sample in acetonitrile after sonification has lasted around 15 h. The sample has then been filtered on a glass filter with a porosity of 0.45 μm before the analysis.

TABLE 2

Dental adhesive composition A292, batch LAN 21-77-1

| Component | wt-in [g] | wt [%] |
|---|---|---|
| compounds having at least one polymerizable double bond including PENTA, and BADEP | 3.1035 | 62.0719 |
| iso-propanol | 0.8406 | 16.8010 |
| water | 1.0535 | 21.1271 |
| SUM | 4.9976 | 100.0000 |

PENTA = Dipentaerythritol pentaacrylate phosphate CAS 87699-25-0
BADEP = N,N'-1,3-propane diylbis[N-ethyl-2-propenamide]

The HPLC analysis of the extraction of A292+1 wt % DPPS photopolymer in acetonitrile has not shown any band characteristic of the DPPS product. A limit value of 2 ppm has been calculated as the maximal amount of extractable DPPS in the photopolymer but it is probably even lower.

Application Example 2: Dental Adhesive Composition

Figure 11A:
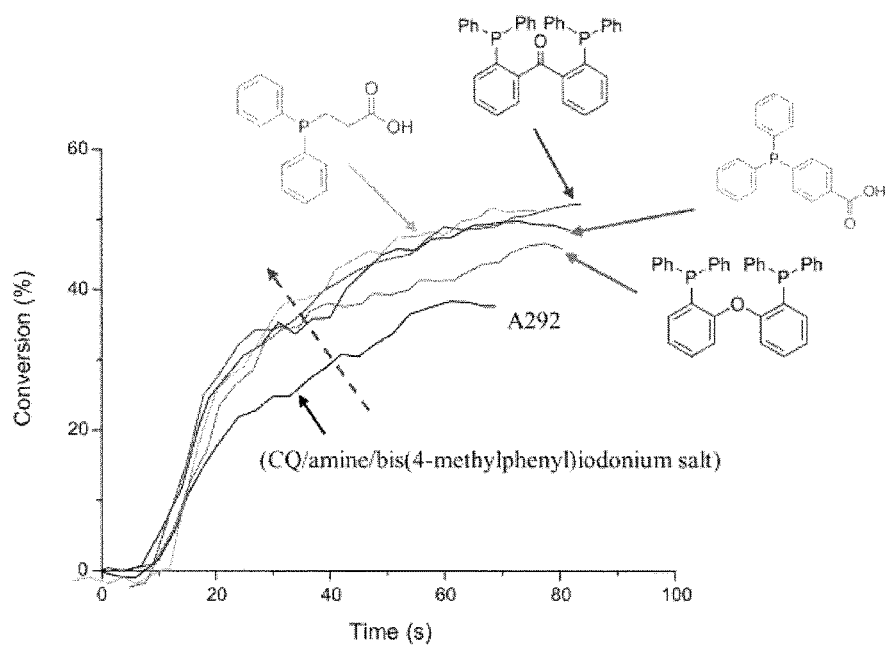
FIG. 11A shows polymerization profiles of a dental adhesive A292 under air upon a SmartLite® Focus exposure without or with different phosphines (1% w/w).
Figure 11B:
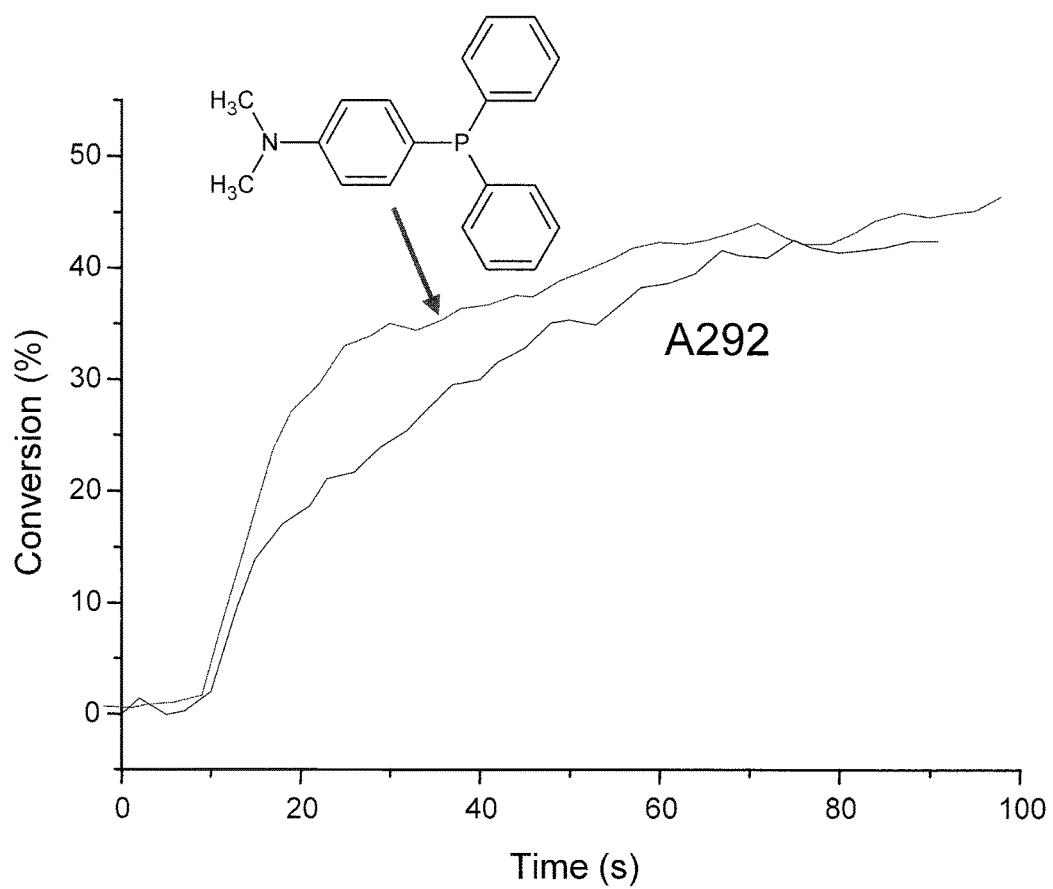
FIG. 11B shows polymerization profiles of a dental adhesive A292 under air upon a SmartLite® Focus exposure, an amino derivative of TPP (1% w/w) was used as co-initiator in replacement of EDB showing the better initiating ability for this amino derivative of TPP.

An adhesive formulation (A292; composition given in Table 2) can be polymerized upon a SmartLite Focus exposure (see the emission spectrum in FIG. 1). The adhesive films (13 μm thick) deposited on a BaF$_2$ pellet were irradiated under air. The evolution of the double bond content was continuously followed by real time FTIR spectroscopy (JASCO FTIR 4100) at about 1225 cm$^{-1}$. Different phosphines were used as additive in this reference adhesive A292. Remarkably for the different investigated phosphines, a huge improvement of the polymerization profiles was found even for 1% in weight (FIG. 11A and FIG. 11B).

Example 14

Figure 12:
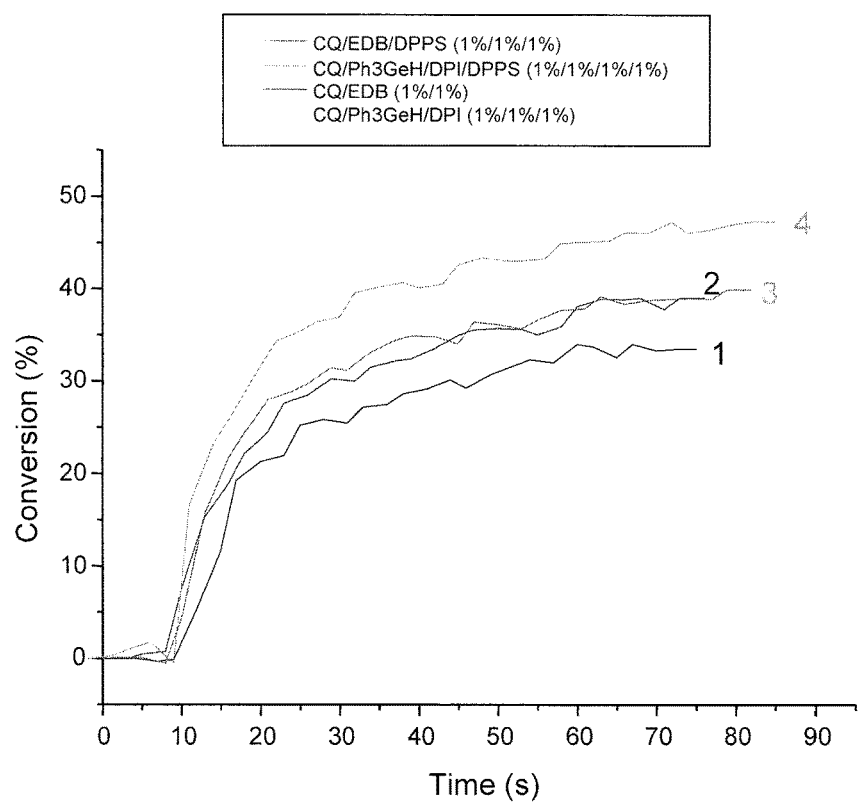
FIG. 12 shows photopolymerization profiles of UDMA upon a SmartLite Focus exposure (under air) for different initiating systems (thickness ~25 µm).

DPPS is a suitable sensitizer in presence of EDB (FIG. 12, curve 2 vs. curve 1); However, in presence of $R_3$GeH based initiating systems (FIG. 12, curve 4 vs. curve 3), it is found that the photoinitiating polymerization ability for UDMA upon a SmartLite Foucs exposure under air follows the trend: CQ/EDB<CQ/EDB/DPPS<CQ/Ph$_3$GeH/DPI<CQ/Ph$_3$GeH/DPI/DPPS (FIG. 12). From these results, the presence of DPPS clearly improves the polymerization initiating ability of the CQ/EDB and CQ/Ph$_3$GeH/DPI system, respectively.

The invention claimed is:

1. A dental composition comprising
   (a) one or more compounds having at least one polymerizable double bond;
   (b) a polymerization initiator system comprising
      (b1) a sensitizer; and
      (b2) an aromatic tertiary phosphine compound of the following formula (I):

Z—R  (I)

wherein
   Z is a group of the following formula (II)

$R^1$(Ar)P—  (II)

wherein
      $R^1$ represents a substituted or unsubstituted hydrocarbyl group;
      Ar represents a substituted or unsubstituted aryl or heteroaryl group;
      R is an aryl group, substituted by one or more groups selected from a hydroxyl group, an amino group, a —$NR^2R^3$ group (wherein $R^2$ and $R^3$, which may be the same or different, are selected from $C_{1-6}$ alkyl groups), a carboxyl group, and a group having a polymerizable double bond;
      wherein the group $R^1$ and Ar may be substituted by one or more groups selected from a hydroxyl group, an oxo group, a —$NR^2R^3$ group (wherein $R^2$ and $R^3$, which may be the same or different, are selected from a hydrogen atom and $C_{1-6}$ alkyl groups), a carboxyl group, and a group having a polymerizable double bond;
      wherein the sensitizer is an 1,2-diketone or a phosphine oxide.

2. The dental composition according to claim 1, wherein the polymerization initiator system further comprises
   (b3) an electron-donor.

3. The dental composition according to claim 1, wherein $R^1$ and Ar independently are aromatic hydrocarbyl groups selected from a phenyl group, a napthyl group, a tolyl group, a xylyl group, and a styryl group.

4. The dental composition according to claim 2, wherein the electron-donor is a tertiary amine compound.

5. The dental composition according to claim 2, wherein the polymerization initiator system comprises component (b1), (b2), and (b3) in a molar ratio ((b1):(b2):(b3)) of 1:(0.1 to 3.0):(0.0 to 3.0).

6. The dental composition according to claim 1, which further comprises a solvent and/or a particulate filler.

7. The dental composition according to claim 1, wherein the dental composition is a dental restorative or dental prosthetic composition.

8. The dental composition according to claim 7, where the dental composition is selected from a dental adhesive composition, a dental composite composition, a resin modified dental cement, a pit and fissure sealer, a desensitizer and a varnish.

9. The dental composition according to claim 1, wherein the aromatic phosphine compound is a compound of formula (I) wherein Z is a group of the following formula (III):

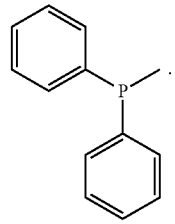

10. A polymerization initiator system comprising: (i) an aromatic phosphine compound of the following formula (I)

Z—R  (I)

wherein
    Z is a group of the following formula (II)

$R^1$(Ar)P—  (II)

wherein
    $R^1$ represents a substituted or unsubstituted hydrocarbyl group;
    Ar represents a substituted or unsubstituted aryl group;
    R is an aryl group, substituted by one or more groups selected from a hydroxyl group, an amino group, a —$NR^2R^3$ group (wherein $R^2$ and $R^3$, which may be the same or different, are selected from $C_{1-6}$ alkyl groups), a carboxyl group, and a group having a polymerizable double bond;
    wherein the group $R^1$ and Ar may be substituted by one or more groups selected from a hydroxyl group, a —$NR^2R^3$ group (wherein $R^2$ and $R^3$, which may be the same or different, are selected from a hydrogen atom and $C_{1-6}$ alkyl groups), a carboxyl group, and a group having a polymerizable double bond, and
    (ii) a sensitizer selected from an 1,2-diketone
    for use in the preparation of a dental composition.

11. The polymerization initiator system according to claim 10, wherein the aromatic phosphine is 4-(diphenylphosphino)styrene.

12. The dental composition according to claim 2, wherein the electron-donor (b3) is a compound of the following formula (IV):

L-H  (IV)

wherein L is a moiety of the following formula (V)

$R^aR^bR^cX$—  (V)

wherein
    X represents Si, Ge, or Sn and
    $R^a$ represents a hydrogen atom, an organic moiety or a different moiety L;
    $R^b$ and $R^c$
    which are independent from each other, represent an organic moiety.

13. The dental composition according to claim 12, which comprises as sensitizer a combination of
    (b1-a) a first sensitizer selected from an 1,2-diketone; and
    (b1-b) a second sensitizer selected from iodonium salts.

* * * * *